(12) United States Patent
Noda et al.

(10) Patent No.: US 7,857,781 B2
(45) Date of Patent: Dec. 28, 2010

(54) INDWELLING HEAT EXCHANGE CATHETER AND METHOD OF USING SAME

(75) Inventors: Wayne A. Noda, Mission Viejo, CA (US); Mike L. Jones, Capistrano Beach, CA (US); Scott M. Evans, Santa Ana, CA (US); Blair D. Walker, Mission Viejo, CA (US); William J. Worthen, Coto de Caza, CA (US); Yves Pierre Gobin, Los Angeles, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 783 days.

(21) Appl. No.: 11/129,980

(22) Filed: May 16, 2005

(65) Prior Publication Data

US 2005/0222653 A1   Oct. 6, 2005

Related U.S. Application Data

(63) Continuation of application No. 09/946,835, filed on Sep. 4, 2001, now Pat. No. 6,893,419, which is a continuation of application No. 09/133,813, filed on Aug. 13, 1998, now Pat. No. 6,338,727, which is a continuation-in-part of application No. 09/063,984, filed on Apr. 21, 1998, now Pat. No. 6,126,684.

(51) Int. Cl.
*A61M 37/00* (2006.01)

(52) U.S. Cl. ............... 604/6.13; 604/95.03; 604/96.01; 604/101.01; 604/101.03; 604/101.05; 604/102.01; 604/102.02; 604/102.03; 604/103.07; 604/113; 604/43; 604/23; 604/104; 604/105; 604/106; 604/114; 604/264; 604/291; 604/523; 606/20; 606/21; 606/22; 606/23; 606/24; 606/25; 606/26; 606/27; 606/28; 607/113; 607/105; 607/106; 607/108; 607/104; 607/109; 607/110; 607/111; 607/112; 607/114; 607/96; 128/898

(58) Field of Classification Search ............... 604/6.13, 604/43, 23, 104–106, 113–114, 264, 291, 604/523, 95.03, 95.01, 101.01, 101.03, 101.05, 604/102.01, 102.02, 102.03, 103.07, 96.01, 604/6.16; 606/20–28; 607/104–114, 96; 128/898

See application file for complete search history.

(56) References Cited

U.S. PATENT DOCUMENTS

| | | |
|---|---|---|
| 2,308,484 A | 1/1943 | Armin at al. |
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,125,096 A * | 3/1964 | Etal .......................... 607/105 |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson et al. |
| 3,604,419 A | 9/1971 | Diskin et al. |
| 3,612,175 A | 10/1971 | Ford at al. |
| 3,674,031 A | 7/1972 | Weiche |
| 3,696,813 A | 10/1972 | Wallach |
| 3,865,116 A | 2/1975 | Brooks |
| 3,888,259 A | 6/1975 | Miley |
| 3,971,383 A | 7/1976 | Van Gerven |

| | | | | | | |
|---|---|---|---|---|---|---|
| 4,038,519 A | 7/1977 | Foucras | | 5,014,695 A | 5/1991 | Benak et al. |
| 4,111,209 A | 9/1978 | Wolvek et al. | | 5,018,521 A | 5/1991 | Campbell |
| 4,153,048 A | 5/1979 | Magrini | | 5,019,075 A | 5/1991 | Spears et al. |
| 4,160,455 A | 7/1979 | Law | | 5,024,668 A | 6/1991 | Peters et al. |
| 4,190,033 A | 2/1980 | Foti | | 5,030,210 A | 7/1991 | Alchas |
| 4,216,767 A | 8/1980 | Aoshiro | | 5,041,089 A | 8/1991 | Mueller et al. |
| 4,231,425 A | 11/1980 | Engstom | | 5,046,497 A | 9/1991 | Millar |
| 4,241,729 A | 12/1980 | Aoshiro | | 5,078,713 A | 1/1992 | Varney |
| 4,246,932 A | 1/1981 | Raines | | 5,089,260 A | 2/1992 | Hunter et al. |
| 4,275,734 A | 6/1981 | Mitchiner | | 5,092,841 A | 3/1992 | Spears |
| 4,298,006 A | 11/1981 | Parks | | 5,106,360 A | 4/1992 | Ishwara et al. |
| 4,318,722 A | 3/1982 | Altman | | 5,106,368 A | 4/1992 | Uldall et al. |
| 4,323,071 A | 4/1982 | Simpson et al. | | 5,108,390 A | 4/1992 | Potocky et al. |
| 4,378,797 A | 4/1983 | Osterholm | | RE33,911 E | 5/1992 | Samson et al. |
| 4,427,009 A | 1/1984 | Wells et al. | | 5,110,721 A | 5/1992 | Anaise et al. |
| 4,445,500 A | 5/1984 | Osterholm | | 5,112,301 A | 5/1992 | Fenton, Jr. et al. |
| 4,445,886 A | 5/1984 | Osterholm | | 5,112,438 A | 5/1992 | Bowers |
| 4,464,172 A | 8/1984 | Lichtenstein | | 5,117,822 A | 6/1992 | Laghi |
| 4,470,407 A | 9/1984 | Hussein | | 5,147,355 A | 9/1992 | Friedman et al. |
| 4,483,341 A | 11/1984 | Witteles | | 5,147,385 A | 9/1992 | Beck et al. |
| 4,484,586 A | 11/1984 | McMickle et al. | | 5,149,321 A | 9/1992 | Klatz et al. |
| 4,497,890 A | 2/1985 | Helbert | | 5,150,706 A | 9/1992 | Cox et al. |
| 4,502,286 A | 3/1985 | Okada et al. | | 5,151,100 A * | 9/1992 | Abele et al. .................. 606/28 |
| 4,540,402 A | 9/1985 | Aigner | | 5,156,151 A | 10/1992 | Imran |
| 4,569,355 A | 2/1986 | Bitterly | | 5,180,364 A | 1/1993 | Ginsburg |
| 4,581,017 A | 4/1986 | Sahota | | 5,190,539 A | 3/1993 | Fletcher et al. |
| 4,602,642 A | 7/1986 | O'Hara et al. | | 5,191,883 A | 3/1993 | Lennox et al. |
| 4,655,746 A | 4/1987 | Daniels et al. | | 5,196,024 A | 3/1993 | Barath |
| 4,661,094 A | 4/1987 | Simpson | | 5,207,640 A | 5/1993 | Hattler ........................ 604/28 |
| 4,662,383 A | 5/1987 | Sogawa et al. | | 5,211,631 A | 5/1993 | Sheaff |
| 4,672,962 A | 6/1987 | Hershenson | | 5,230,862 A | 7/1993 | Berry et al. ................... 422/48 |
| 4,686,085 A | 8/1987 | Osterholm | | 5,234,405 A | 8/1993 | Klatz et al. |
| 4,701,166 A | 10/1987 | Groshong et al. | | 5,236,908 A | 8/1993 | Gruber et al. |
| 4,705,501 A | 11/1987 | Wigners et al. | | 5,239,999 A | 8/1993 | Imran |
| 4,706,671 A * | 11/1987 | Weinrib ...................... 606/159 | | 5,241,951 A | 9/1993 | Mason et al. |
| 4,731,072 A | 3/1988 | Aid | | 5,246,421 A | 9/1993 | Saab |
| 4,739,492 A | 4/1988 | Cochran | | 5,248,312 A | 9/1993 | Langberg |
| 4,745,922 A | 5/1988 | Taylor | | 5,250,070 A | 10/1993 | Parodi |
| 4,747,826 A | 5/1988 | Sassano | | 5,254,091 A * | 10/1993 | Aliahmad et al. ...... 604/103.06 |
| 4,748,979 A | 6/1988 | Hershenson | | 5,257,977 A | 11/1993 | Eshel |
| 4,750,493 A | 6/1988 | Brader | | 5,264,260 A | 11/1993 | Saab |
| 4,754,752 A | 7/1988 | Ginsburg et al. | | 5,267,341 A | 11/1993 | Shearin |
| 4,762,129 A | 8/1988 | Bonzel | | 5,269,158 A | 12/1993 | Bitter et al. |
| 4,762,130 A * | 8/1988 | Fogarty et al. ............... 606/159 | | 5,269,369 A | 12/1993 | Faghri |
| 4,769,005 A | 9/1988 | Ginsburg et al. | | 5,269,749 A | 12/1993 | Koturov |
| 4,781,799 A | 11/1988 | Herbert, Jr. et al. | | 5,269,758 A | 12/1993 | Taheri |
| 4,796,640 A | 1/1989 | Webler | | 5,271,743 A | 12/1993 | Hattler ........................ 604/26 |
| 4,804,358 A | 2/1989 | Karacher et al. | | 5,279,299 A | 1/1994 | Imran |
| 4,817,624 A | 4/1989 | Newbower | | 5,281,213 A | 1/1994 | Midler et al. |
| 4,819,655 A | 4/1989 | Webler | | 5,281,215 A | 1/1994 | Milder |
| 4,820,349 A | 4/1989 | Saab | | 5,306,261 A | 4/1994 | Alliger et al. |
| 4,840,617 A | 6/1989 | Osterholm | | 5,308,356 A * | 5/1994 | Blackshear et al. ......... 606/194 |
| 4,857,054 A | 8/1989 | Helfer | | 5,310,440 A | 5/1994 | Zingher |
| 4,860,744 A | 8/1989 | Johnson et al. | | 5,322,514 A | 6/1994 | Steube et al. |
| 4,883,455 A | 11/1989 | Leonard | | 5,322,515 A | 6/1994 | Karas et al. |
| 4,892,095 A | 1/1990 | Nakhgevany | | 5,322,518 A | 6/1994 | Schneider et al. |
| 4,892,519 A | 1/1990 | Songer et al. | | 5,326,165 A | 7/1994 | Walthall et al. |
| 4,894,164 A | 1/1990 | Polaschegg | | 5,326,166 A | 7/1994 | Walthall et al. |
| 4,899,741 A | 2/1990 | Bentley et al. | | 5,330,435 A | 7/1994 | Vailancourt |
| 4,904,237 A | 2/1990 | Janese | | 5,330,438 A | 7/1994 | Gollobin et al. |
| 4,909,252 A | 3/1990 | Goldberger | | 5,330,519 A | 7/1994 | Mason et al. |
| 4,920,963 A | 5/1990 | Brader | | 5,334,193 A | 8/1994 | Nardella |
| 4,941,475 A | 7/1990 | Williams et al. | | 5,340,290 A | 8/1994 | Clemens |
| 4,951,677 A | 8/1990 | Crowlet et al. | | 5,342,181 A | 8/1994 | Schock et al. |
| 4,964,409 A | 10/1990 | Tremulis | | 5,342,301 A | 8/1994 | Saab |
| 4,973,493 A | 11/1990 | Guire | | 5,342,621 A | 8/1994 | Eury |
| 4,976,691 A | 12/1990 | Sahota | | 5,344,436 A | 9/1994 | Fontenot et al. |
| 4,979,959 A | 12/1990 | Guire | | 5,344,740 A | 9/1994 | Iwasawa et al. |
| 4,995,863 A | 2/1991 | Nichols et al. | | 5,354,186 A | 10/1994 | Murtuza et al. |
| 5,000,664 A | 3/1991 | Lawless et al. | | 5,354,272 A | 10/1994 | Swendson et al. |
| 5,000,734 A | 3/1991 | Boussignac et al. | | 5,358,486 A | 10/1994 | Saab |
| 5,002,531 A | 3/1991 | Bonzel | | 5,364,364 A | 11/1994 | Kasvikis et al. |
| 5,011,488 A * | 4/1991 | Ginsburg ..................... 606/159 | | 5,365,750 A | 11/1994 | Greenthal |

| | | | |
|---|---|---|---|
| 5,368,591 A | 11/1994 | Lennox et al. | |
| 5,383,854 A | 1/1995 | Safar et al. | |
| 5,383,856 A | 1/1995 | Bersin | |
| 5,383,918 A | 1/1995 | Panetta | |
| 5,395,314 A | 3/1995 | Klatz et al. | |
| 5,395,331 A | 3/1995 | O'Neil et al. | |
| 5,403,281 A | 4/1995 | O'Neil et al. | |
| 5,415,634 A * | 5/1995 | Glynn et al. | 604/103.08 |
| 5,417,686 A | 5/1995 | Peterson et al. | |
| 5,423,745 A | 6/1995 | Todd et al. | |
| 5,423,807 A | 6/1995 | Milder | |
| 5,433,740 A | 7/1995 | Yamaguchi | |
| 5,437,673 A | 8/1995 | Baust et al. | |
| 5,443,456 A | 8/1995 | Alliger et al. | |
| 5,450,516 A | 9/1995 | Pasquali et al. | 385/115 |
| 5,458,574 A | 10/1995 | Machold et al. | |
| 5,462,521 A | 10/1995 | Brucker et al. | |
| 5,464,437 A * | 11/1995 | Reid et al. | 607/101 |
| 5,470,659 A | 11/1995 | Baumgart et al. | 428/398 |
| 5,484,384 A * | 1/1996 | Fearnot | 600/3 |
| 5,486,204 A | 1/1996 | Clifton | |
| 5,486,208 A * | 1/1996 | Ginsburg | 607/106 |
| 5,496,271 A | 3/1996 | Burton et al. | |
| 5,499,973 A | 3/1996 | Saab | |
| 5,520,682 A | 5/1996 | Baust et al. | |
| 5,531,776 A | 7/1996 | Ward et al. | |
| 5,536,247 A | 7/1996 | Thorton | |
| 5,540,659 A * | 7/1996 | Teirstein | 604/104 |
| 5,545,133 A | 8/1996 | Burns et al. | |
| 5,545,708 A | 8/1996 | Onwunaka et al. | |
| 5,549,559 A | 8/1996 | Eshel | |
| 5,554,119 A | 9/1996 | Harrison et al. | |
| 5,558,644 A | 9/1996 | Boyd et al. | |
| 5,569,195 A | 10/1996 | Saab | |
| 5,573,532 A | 11/1996 | Chang et al. | |
| 5,578,008 A | 11/1996 | Hara | |
| 5,584,804 A | 12/1996 | Klatz et al. | |
| 5,588,438 A | 12/1996 | McKown et al. | |
| 5,591,162 A | 1/1997 | Fletcher et al. | |
| 5,620,480 A | 4/1997 | Rudie | |
| 5,622,182 A | 4/1997 | Jaffe | |
| 5,624,342 A | 4/1997 | Younger | |
| 5,624,392 A * | 4/1997 | Saab | 604/43 |
| 5,630,837 A | 5/1997 | Crowley | |
| 5,643,171 A * | 7/1997 | Bradshaw et al. | 600/1 |
| 5,643,197 A | 7/1997 | Brucker et al. | |
| 5,647,051 A | 7/1997 | Neer | |
| 5,653,692 A | 8/1997 | Masterson et al. | |
| 5,676,693 A | 10/1997 | LaFontaine | |
| 5,709,654 A | 1/1998 | Klatz et al. | |
| 5,713,941 A | 2/1998 | Robins et al. | |
| 5,716,386 A | 2/1998 | Ward et al. | |
| 5,725,949 A | 3/1998 | Pasquali et al. | 428/398 |
| 5,733,318 A | 3/1998 | Augustine | |
| 5,733,319 A | 3/1998 | Neilson et al. | |
| 5,735,809 A | 4/1998 | Gorsuch | 428/364 |
| 5,755,690 A | 5/1998 | Saab | 604/96 |
| 5,782,740 A * | 7/1998 | Schneiderman | 600/1 |
| 5,787,715 A | 8/1998 | Dobak, III et al. | |
| 5,797,878 A | 8/1998 | Bleam | |
| 5,799,661 A | 9/1998 | Boyd et al. | |
| 5,800,480 A | 9/1998 | Augustine et al. | |
| 5,800,483 A | 9/1998 | Vought | |
| 5,800,486 A | 9/1998 | Thome | |
| 5,800,488 A | 9/1998 | Crockett | |
| 5,800,516 A | 9/1998 | Fine et al. | |
| 5,807,391 A | 9/1998 | Wijkamp | |
| 5,820,593 A | 10/1998 | Safar et al. | |
| 5,824,030 A | 10/1998 | Yang et al. | |
| 5,827,222 A | 10/1998 | Klatz et al. | |
| 5,827,237 A | 10/1998 | Macoviak et al. | |
| 5,827,269 A | 10/1998 | Saadat | |
| 5,833,671 A | 11/1998 | Macoviak et al. | |
| 5,833,673 A | 11/1998 | Ockuly et al. | |
| 5,834,465 A | 11/1998 | Olney | |
| 5,837,003 A | 11/1998 | Ginsburg | 607/106 |
| 5,861,021 A | 1/1999 | Thome et al. | |
| 5,868,735 A | 2/1999 | Lafontaine | |
| 5,871,468 A | 2/1999 | Kramer et al. | |
| 5,871,526 A | 2/1999 | Gibbs et al. | |
| 5,873,835 A | 2/1999 | Hastings et al. | |
| 5,876,667 A | 3/1999 | Gremel et al. | 604/4 |
| 5,879,316 A | 3/1999 | Safar et al. | |
| 5,879,329 A | 3/1999 | Ginsburg | 604/93 |
| 5,891,027 A | 4/1999 | Tu et al. | |
| 5,891,094 A | 4/1999 | Masterson et al. | |
| 5,899,899 A | 5/1999 | Arless et al. | |
| 5,901,783 A | 5/1999 | Dobak, III et al. | |
| 5,902,268 A | 5/1999 | Saab | |
| 5,902,299 A * | 5/1999 | Jayaraman | 606/20 |
| 5,906,588 A | 5/1999 | Safar et al. | |
| 5,906,594 A | 5/1999 | Scarfone et al. | |
| 5,906,636 A | 5/1999 | Casscells, III et al. | |
| 5,910,101 A | 6/1999 | Andrews et al. | |
| 5,910,104 A | 6/1999 | Dobak, III et al. | |
| 5,913,854 A | 6/1999 | Maguire et al. | |
| 5,913,856 A | 6/1999 | Chia et al. | |
| 5,913,885 A | 6/1999 | Klatz et al. | |
| 5,913,886 A | 6/1999 | Soloman | |
| 5,916,242 A | 6/1999 | Schwartz | |
| 5,957,917 A | 9/1999 | Doiron et al. | |
| 5,957,963 A * | 9/1999 | Dobak, III | 607/104 |
| 5,964,751 A | 10/1999 | Amplatz et al. | |
| 5,967,976 A | 10/1999 | Larsen et al. | |
| 5,968,009 A | 10/1999 | Siman | |
| 5,971,979 A | 10/1999 | Joye et al. | |
| 5,989,238 A | 11/1999 | Ginsburg | 604/93 |
| 6,004,289 A | 12/1999 | Saab | 604/96 |
| 6,007,692 A | 12/1999 | Herbert et al. | |
| 6,011,995 A | 1/2000 | Guglielmi et al. | |
| 6,019,783 A | 2/2000 | Philips | 607/105 |
| 6,022,336 A | 2/2000 | Zadno-Azizi et al. | |
| 6,024,740 A | 2/2000 | Lesh et al. | |
| 6,033,383 A | 3/2000 | Ginsburg | |
| 6,042,559 A | 3/2000 | Dobak | 604/7 |
| 6,051,019 A * | 4/2000 | Dobak, III | 607/104 |
| 6,063,101 A | 5/2000 | Jacobsen et al. | |
| 6,096,068 A | 8/2000 | Dobak | 607/105 |
| 6,110,168 A | 8/2000 | Ginsburg | 606/27 |
| 6,110,192 A * | 8/2000 | Ravenscroft et al. | 606/194 |
| 6,126,684 A * | 10/2000 | Gobin et al. | 607/113 |
| 6,146,411 A | 11/2000 | Noda | 607/105 |
| 6,146,814 A | 11/2000 | Millet | |
| 6,149,670 A | 11/2000 | Worthen | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak | 607/106 |
| 6,165,207 A | 12/2000 | Balding | 607/105 |
| 6,182,666 B1 | 2/2001 | Dobak, III | |
| 6,190,354 B1 | 2/2001 | LaFontaine | |
| 6,194,899 B1 | 2/2001 | Ishihara et al. | |
| 6,196,996 B1 * | 3/2001 | Teirstein | 604/104 |
| 6,210,312 B1 * | 4/2001 | Nagy | 600/3 |
| 6,224,624 B1 | 5/2001 | Lasheras | 607/105 |
| 6,231,594 B1 | 5/2001 | Dae | 607/96 |
| 6,231,595 B1 * | 5/2001 | Dobak, III | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |
| 6,251,093 B1 | 6/2001 | Valley et al. | |
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,261,312 B1 | 7/2001 | Dobak, III et al. | |
| 6,264,679 B1 | 7/2001 | Keller | 607/105 |
| 6,277,143 B1 | 8/2001 | Klatz et al. | |

| | | | | | | |
|---|---|---|---|---|---|---|
| 6,287,326 B1 | 9/2001 | Pecor | 607/105 | 6,595,967 B2 | 7/2003 | Kramer | 604/523 |
| 6,290,697 B1 | 9/2001 | Tu et al. | | 6,599,230 B2 * | 7/2003 | Hastings et al. | 600/3 |
| 6,290,717 B1 | 9/2001 | Philips | 607/113 | 6,599,312 B2 | 7/2003 | Dobak | 607/105 |
| 6,295,990 B1 | 10/2001 | Lewis et al. | | 6,602,243 B2 | 8/2003 | Noda | 604/544 |
| 6,299,599 B1 * | 10/2001 | Pham et al. | 604/113 | 6,602,276 B2 | 8/2003 | Dobak | 607/105 |
| 6,306,161 B1 | 10/2001 | Ginsburg | 607/106 | 6,607,517 B1 | 8/2003 | Dae | 604/31 |
| 6,312,452 B1 | 11/2001 | Dobak | 607/105 | 6,610,083 B2 * | 8/2003 | Keller et al. | 607/105 |
| 6,315,754 B1 | 11/2001 | Daoud et al. | | 6,620,130 B1 | 9/2003 | Ginsburg | 604/113 |
| 6,315,995 B1 | 11/2001 | Pinsky et al. | | 6,620,131 B2 | 9/2003 | Pham | 604/113 |
| 6,316,403 B1 | 11/2001 | Pinsky et al. | | 6,620,188 B1 | 9/2003 | Ginsburg | 607/106 |
| 6,319,248 B1 | 11/2001 | Nahon | | 6,620,189 B1 | 9/2003 | MacHold et al. | 607/106 |
| 6,325,818 B1 | 12/2001 | Werneth | 607/105 | 6,623,516 B2 | 9/2003 | Saab | 607/105 |
| 6,336,911 B1 | 1/2002 | Westerbeck | | 6,635,076 B1 | 10/2003 | Ginsburg | 607/106 |
| 6,338,727 B1 | 1/2002 | Noda | 604/113 | 6,641,602 B2 | 11/2003 | Balding | 607/105 |
| 6,354,099 B1 | 3/2002 | Bieberich | | 6,641,603 B2 | 11/2003 | Walker | 607/105 |
| 6,364,899 B1 | 4/2002 | Dobak | 607/113 | 6,645,234 B2 | 11/2003 | Evans | 607/113 |
| 6,368,304 B1 * | 4/2002 | Aliberto et al. | 604/113 | 6,648,906 B2 | 11/2003 | Lasheras | 607/105 |
| 6,379,378 B1 | 4/2002 | Werneth | 607/96 | 6,648,908 B2 | 11/2003 | Dobak | 607/105 |
| 6,383,210 B1 | 5/2002 | Magers et al. | 607/105 | 6,652,565 B1 | 11/2003 | Shimada | 607/113 |
| 6,393,320 B2 | 5/2002 | Lasersohn | 607/3 | 6,656,209 B1 | 12/2003 | Ginsburg | 607/106 |
| 6,405,080 B1 | 6/2002 | Lasersohn | 607/3 | 6,660,028 B2 | 12/2003 | Magers | 607/105 |
| 6,409,747 B1 * | 6/2002 | Gobin et al. | 607/113 | 6,673,098 B1 | 1/2004 | MacHold | 607/106 |
| 6,416,533 B1 * | 7/2002 | Gobin et al. | 607/113 | 6,676,688 B2 | 1/2004 | Dobak | 607/105 |
| 6,419,643 B1 | 7/2002 | Shimada | 600/323 | 6,676,689 B2 | 1/2004 | Dobak | 607/105 |
| 6,428,563 B1 | 8/2002 | Keller | 607/105 | 6,676,690 B2 | 1/2004 | Werneth | 607/105 |
| 6,432,124 B1 | 8/2002 | Worthen | 607/105 | 6,679,906 B2 | 1/2004 | Hammack | |
| 6,436,130 B1 | 8/2002 | Philips | 607/105 | 6,679,907 B2 | 1/2004 | Dobak | 607/105 |
| 6,436,131 B1 | 8/2002 | Ginsburg | 607/106 | 6,682,551 B1 | 1/2004 | Worthen | 607/105 |
| 6,440,158 B1 | 8/2002 | Saab | 604/105 | 6,685,732 B2 | 2/2004 | Kramer | 607/106 |
| 6,447,474 B1 | 9/2002 | Balding | 604/66 | 6,685,733 B1 | 2/2004 | Dae | 607/105 |
| 6,450,987 B1 | 9/2002 | Kramer | 604/523 | 6,692,488 B2 | 2/2004 | Dobak | 606/21 |
| 6,450,990 B1 | 9/2002 | Walker | 604/113 | 6,692,519 B1 | 2/2004 | Hayes | 607/105 |
| 6,451,045 B1 | 9/2002 | Walker | 607/105 | 6,695,873 B2 | 2/2004 | Dobak | 607/105 |
| 6,454,775 B1 * | 9/2002 | Demarais et al. | 606/128 | 6,695,874 B2 | 2/2004 | MacHold | 607/106 |
| 6,454,792 B1 | 9/2002 | Noda | 607/105 | 6,699,268 B2 | 3/2004 | Kordis | 607/113 |
| 6,454,793 B1 | 9/2002 | Evans | 607/105 | 6,702,783 B1 | 3/2004 | Dae | 604/113 |
| 6,458,150 B1 | 10/2002 | Evans | 607/105 | 6,702,839 B1 | 3/2004 | Dae | 607/96 |
| 6,460,544 B1 | 10/2002 | Worthen | 607/105 | 6,702,840 B2 * | 3/2004 | Keller et al. | 607/105 |
| 6,464,716 B1 | 10/2002 | Dobak | 607/105 | 6,702,841 B2 | 3/2004 | Nest | 607/105 |
| 6,468,296 B1 | 10/2002 | Dobak | 607/105 | 6,702,842 B2 | 3/2004 | Dobak | 607/105 |
| 6,471,717 B1 | 10/2002 | Dobak | 607/105 | 6,706,060 B2 | 3/2004 | Tzeng | 607/105 |
| 6,475,231 B2 | 11/2002 | Dobak | 607/105 | 6,709,448 B2 | 3/2004 | Walker | 607/105 |
| 6,478,811 B1 | 11/2002 | Dobak | 607/105 | 6,716,188 B2 | 4/2004 | Noda | 604/6.13 |
| 6,478,812 B2 | 11/2002 | Dobak | 607/105 | 6,716,236 B1 | 4/2004 | Tzeng | 607/113 |
| 6,482,226 B1 | 11/2002 | Dobak | 607/104 | 6,719,723 B2 | 4/2004 | Werneth | 604/113 |
| 6,491,039 B1 | 12/2002 | Dobak | 128/898 | 6,719,724 B1 | 4/2004 | Walker | 604/113 |
| 6,491,716 B2 | 12/2002 | Dobak | 607/105 | 6,719,779 B2 | 4/2004 | Daoud | 607/105 |
| 6,494,903 B2 | 12/2002 | Pecor | 607/105 | 6,726,653 B2 * | 4/2004 | Noda et al. | 604/113 |
| 6,497,721 B2 | 12/2002 | Ginsburg | 607/106 | 6,726,708 B2 | 4/2004 | Lasheras | 607/105 |
| 6,516,224 B2 | 2/2003 | Balding et al. | 607/3 | 6,726,710 B2 | 4/2004 | Worthen | 607/105 |
| 6,520,933 B1 | 2/2003 | Evans et al. | 604/103.07 | 6,733,517 B1 | 5/2004 | Collins | 607/105 |
| 6,527,798 B2 | 3/2003 | Ginsburg | 607/106 | 6,740,109 B2 | 5/2004 | Dobak | 607/105 |
| 6,529,775 B2 | 3/2003 | Whitebook | 607/100 | 6,749,585 B2 | 6/2004 | Aliberto | 604/113 |
| 6,530,946 B1 | 3/2003 | Noda | 607/113 | 6,749,625 B2 | 6/2004 | Pompa | 607/105 |
| 6,533,804 B2 | 3/2003 | Dobak | 607/105 | 6,752,786 B2 | 6/2004 | Callister | 604/113 |
| 6,537,271 B1 * | 3/2003 | Murray et al. | 606/21 | 6,755,850 B2 | 6/2004 | Dobak | 607/104 |
| 6,540,771 B2 | 4/2003 | Dobak | 607/105 | 6,755,851 B2 * | 6/2004 | Noda et al. | 607/106 |
| 6,544,282 B1 | 4/2003 | Dae | 607/105 | 6,811,551 B2 | 11/2004 | Dae et al. | |
| 6,551,349 B2 | 4/2003 | Lasheras | 607/105 | 6,942,644 B2 | 9/2005 | Worthen | |
| 6,554,797 B1 | 4/2003 | Worthen | 604/113 | 2001/0001830 A1 | 5/2001 | Dobak, III et al. | |
| 6,558,412 B2 | 5/2003 | Dobak | 607/105 | 2001/0001831 A1 | 5/2001 | Dobak, III et al. | |
| 6,572,538 B2 | 6/2003 | Takase | 600/140 | 2001/0001832 A1 | 5/2001 | Dobak, III et al. | |
| 6,572,638 B1 | 6/2003 | Dae et al. | 607/96 | 2001/0002442 A1 | 5/2001 | Dobak, III | |
| 6,572,640 B1 | 6/2003 | Balding | 607/105 | 2001/0005791 A1 | 6/2001 | Ginsburg et al. | |
| 6,576,001 B2 | 6/2003 | Werneth | 607/96 | 2001/0007951 A1 | 7/2001 | Dobak | 607/106 |
| 6,576,002 B2 | 6/2003 | Dobak | 607/105 | 2001/0008975 A1 | 7/2001 | Dobak, III et al. | |
| 6,581,403 B2 | 6/2003 | Whitebook | 62/434 | 2001/0010011 A1 | 7/2001 | Aliberto et al. | |
| 6,582,398 B1 | 6/2003 | Worthen | 604/113 | 2001/0011184 A1 | 8/2001 | Dobak, III et al. | |
| 6,582,455 B1 | 6/2003 | Dobak | 607/105 | 2001/0011185 A1 | 8/2001 | Dobak, III et al. | |
| 6,582,457 B2 | 6/2003 | Dae | 607/113 | 2001/0014802 A1 | 8/2001 | Tu | |
| 6,585,692 B1 | 7/2003 | Worthen | 604/113 | 2001/0016763 A1 | 8/2001 | Lasheras et al. | |
| 6,585,752 B2 | 7/2003 | Dobak | 607/105 | 2001/0016764 A1 | 8/2001 | Dobak, III | 607/105 |
| 6,589,271 B1 | 7/2003 | Tzeng | 607/113 | 2001/0021865 A1 | 9/2001 | Dobak, III et al. | |

| | | |
|---|---|---|
| 2001/0021866 A1 | 9/2001 | Dobak, III et al. |
| 2001/0029394 A1 | 10/2001 | Dobak, III et al. |
| 2001/0031946 A1 | 10/2001 | Walker et al. |
| 2001/0032003 A1 | 10/2001 | Pecor |
| 2001/0032004 A1 | 10/2001 | Werneth |
| 2001/0037081 A1* | 11/2001 | Heiner .................. 604/23 |
| 2001/0039440 A1 | 11/2001 | Lasheras et al. |
| 2001/0041923 A1 | 11/2001 | Dobak .................. 607/105 |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049495 A1* | 12/2001 | Schwartz .................. 604/113 |
| 2001/0049545 A1 | 12/2001 | Lasersohn et al. |
| 2002/0002394 A1 | 1/2002 | Dobak, III |
| 2002/0004675 A1 | 1/2002 | Lasheras |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin .................. 607/105 |
| 2002/0016621 A1 | 2/2002 | Werneth .................. 607/96 |
| 2002/0022823 A1 | 2/2002 | Luo et al. |
| 2002/0026227 A1 | 2/2002 | Philips |
| 2002/0029016 A1 | 3/2002 | Pham et al. |
| 2002/0029073 A1 | 3/2002 | Schwartz |
| 2002/0032430 A1 | 3/2002 | Luo et al. |
| 2002/0032474 A1 | 3/2002 | Dobak, III et al. |
| 2002/0040717 A1 | 4/2002 | Dobak, III |
| 2002/0045852 A1 | 4/2002 | Saab |
| 2002/0045892 A1 | 4/2002 | Kramer |
| 2002/0045925 A1 | 4/2002 | Keller et al. |
| 2002/0049409 A1 | 4/2002 | Noda et al. |
| 2002/0049484 A1 | 4/2002 | Werneth et al. |
| 2002/0056281 A1 | 5/2002 | Bieberich |
| 2002/0066458 A1 | 6/2002 | Aliberto et al. |
| 2002/0068964 A1 | 6/2002 | Dobak .................. 607/113 |
| 2002/0077665 A1 | 6/2002 | Kordis et al. |
| 2002/0077680 A1 | 6/2002 | Noda .................. 600/549 |
| 2002/0082671 A1 | 6/2002 | Magers et al. |
| 2002/0091378 A1 | 7/2002 | Dobak, III et al. |
| 2002/0091429 A1 | 7/2002 | Dobak .................. 607/105 |
| 2002/0091430 A1 | 7/2002 | Dobak, III et al. |
| 2002/0095200 A1 | 7/2002 | Dobak, III et al. |
| 2002/0095201 A1 | 7/2002 | Worthen et al. |
| 2002/0111616 A1 | 8/2002 | Dea .................. 606/27 |
| 2002/0151946 A1 | 10/2002 | Dobak, III .................. 607/105 |
| 2002/0177804 A1 | 11/2002 | Saab .................. 607/105 |
| 2002/0183692 A1 | 12/2002 | Callister .................. 604/113 |
| 2002/0193738 A1 | 12/2002 | Adzich .................. 604/113 |
| 2002/0193853 A1 | 12/2002 | Worthen et al. .................. 607/105 |
| 2002/0193854 A1 | 12/2002 | Dobak .................. 607/105 |
| 2003/0078641 A1 | 4/2003 | Dobak .................. 607/105 |
| 2003/0114835 A1 | 6/2003 | Noda .................. 604/544 |
| 2003/0144714 A1 | 7/2003 | Dobak .................. 607/104 |
| 2003/0187489 A1 | 10/2003 | Dobak .................. 607/105 |
| 2003/0195465 A1 | 10/2003 | Worthen .................. 604/113 |
| 2003/0195466 A1 | 10/2003 | Pham .................. 604/113 |
| 2003/0195597 A1 | 10/2003 | Keller .................. 607/105 |
| 2003/0216799 A1 | 11/2003 | Worthen .................. 606/27 |
| 2003/0225336 A1 | 12/2003 | Callister .................. 600/505 |
| 2004/0034399 A1 | 2/2004 | Ginsburg .................. 607/106 |
| 2004/0039431 A1 | 2/2004 | Machold |
| 2004/0044388 A1 | 3/2004 | Pham .................. 607/105 |
| 2004/0050154 A1 | 3/2004 | Machold |
| 2004/0054325 A1 | 3/2004 | Ginsburg .................. 604/113 |
| 2004/0073280 A1 | 4/2004 | Dae |
| 2004/0087934 A1 | 5/2004 | Dobak |
| 2004/0102825 A1 | 5/2004 | Daoud |
| 2004/0102826 A1 | 5/2004 | Lasheras |
| 2004/0102827 A1 | 5/2004 | Werneth |
| 2004/0106969 A1 | 6/2004 | Dobak |
| 2004/0111138 A1 | 6/2004 | Bleam .................. 607/105 |
| 2004/0116987 A1 | 6/2004 | Magers |
| 2004/0116988 A1 | 6/2004 | Hammack |
| 2004/0127851 A1 | 7/2004 | Noda .................. 604/503 |
| 2005/0273145 A1 | 12/2005 | Saab |
| 2006/0030910 A1 | 2/2006 | Ginsburg |
| 2008/0046046 A1 | 2/2008 | Ginsburg |
| 2008/0114431 A1 | 5/2008 | Ginsburg |
| 2008/0177231 A1 | 7/2008 | Saab |

FOREIGN PATENT DOCUMENTS

| | | |
|---|---|---|
| EP | 0251745 | 6/1987 |
| JP | 61-263456 | 11/1986 |
| JP | 11-218370 | 8/1999 |
| WO | 9304727 | 3/1993 |
| WO | 9421315 | 9/1994 |
| WO | WO 97/03604 * | 2/1997 |

OTHER PUBLICATIONS

William Worthen, File History of U.S. Appl. No. 10/403,981, filed Mar. 31, 2003 titled, "Method and System for Patent Temperature Management and Central Venous Access", U.S. Patent No. 6,942,644 issued Sep. 13, 2005.

Wayne A. Noda, Scott M. Evans, Mike L. Jones, File History of U.S. Appl. No. 10/138,290, filed May 2, 2002 titled, "Indwelling Heat Exchange Catheter and Method of Using Same", U.S. Patent No. 6,755,851 issued Jun. 29, 2004.

Elbert Tzeng, Peter Barker, Scott M. Evans, Wayne A. Noda, File History of U.S. Appl. No. 10/045,936, filed Oct. 19, 2001 titled, "Intravascular Catheter with Heat Exchange Element Having Inner Inflation Element and Methods of Use", U.S. Patent No, 6,716,236 issued Apr. 6, 2004.

William J. Worthen, File History of U.S. Appl. No. 09/839,747, filed Apr. 19, 2001 titled, "Method and System for Patient Temperature Management and Central Venous Access", U.S. Patent No. 6,585,692 issued Jul. 1, 2003.

U.S. Appl. No. 60/272,442, Worthen et al.

Robert Ginsburg, File History of U.S. Appl. No. 11/044,997 filed Jan. 26, 2005 titled: "Method and Apparatus for Controlling a Patient's Body Temperature by In Situ Blood Temperature Modification".

Mark Saab, File History of U.S. Appl. No. 11/167,036 file Jun. 24, 2005 titled: "Multi-Lumen Heat Transfer Catheters".

Robert Ginsburg, File History of U.S. Appl. No. 11/810,866 filed Jun. 6, 2007 titled: "Method and Endovascular Management of Body Temperature".

Robert Ginsburg, File History of U.S. Appl. No. 11/932,509 file Oct. 31, 2007 titled: "Method and Apparatus for Controlling a Patient's Body Temperature by In Situ Blood Temperature Modification".

Mark A. Saab, File History of U.S. Appl. No. 12/032,455 filed Feb. 15, 2008 titled: "Heat Transfer Catheters and Methods of Making and Using Same".

* cited by examiner

*Primary Examiner*—Tatyana Zalukaeva
*Assistant Examiner*—Ginger T Chapman
(74) *Attorney, Agent, or Firm*—John L. Rogitz

(57) ABSTRACT

A catheter is adapted to exchange heat with a body fluid, such as blood, flowing in a body conduit, such as a blood vessel. The catheter includes a shaft with a heat exchange region disposed at its distal end. This region may include hollow fibers which are adapted to receive a remotely cooled heat exchange fluid preferably flowing in a direction counter to that of the body fluid. The hollow fibers enhance the surface area of contact, as well as the mixing of both the heat exchange fluid and the body fluid. The catheter can be positioned to produce hypothermia in a selective area of the body or alternatively positioned to systemically cool the entire body system.

10 Claims, 19 Drawing Sheets

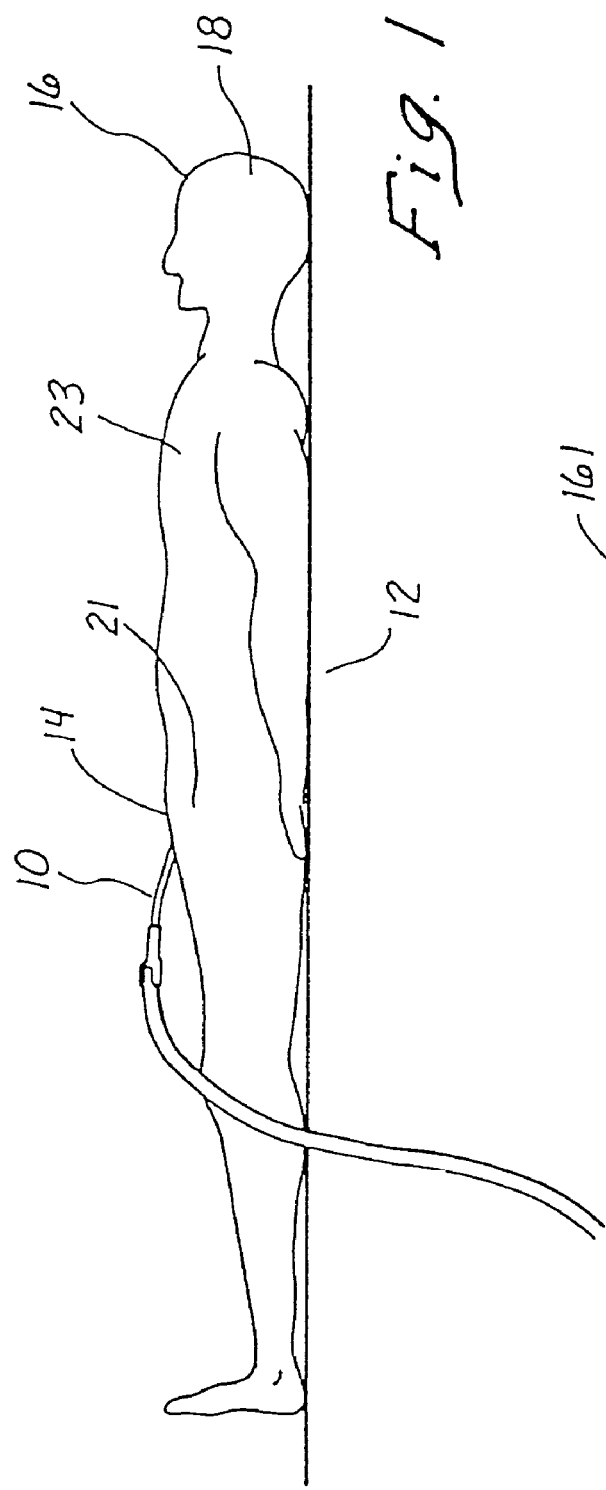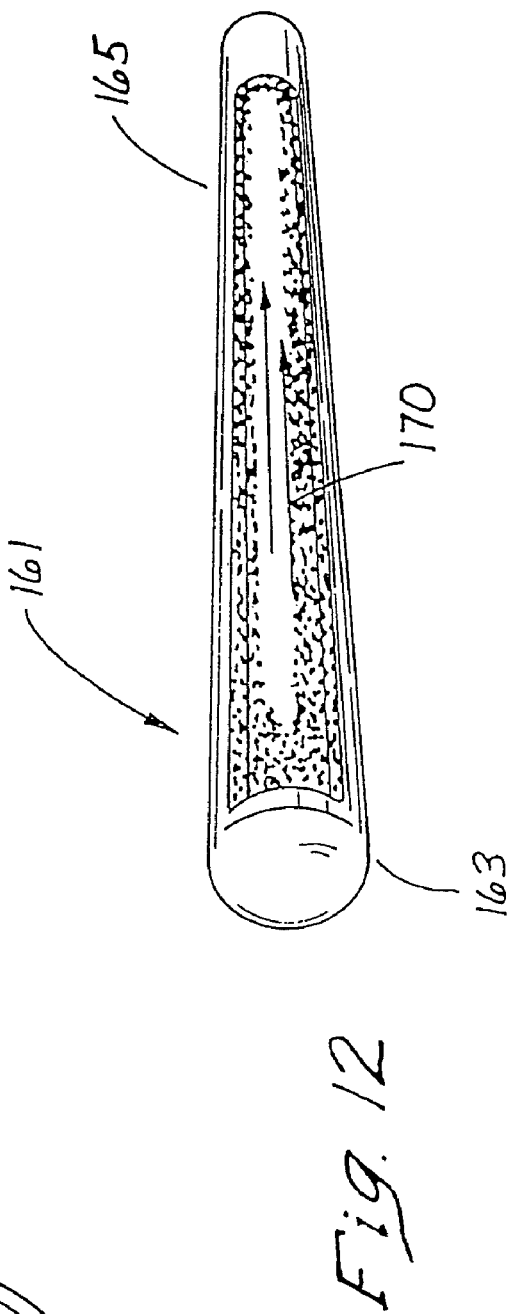
Fig. 1
Fig. 12

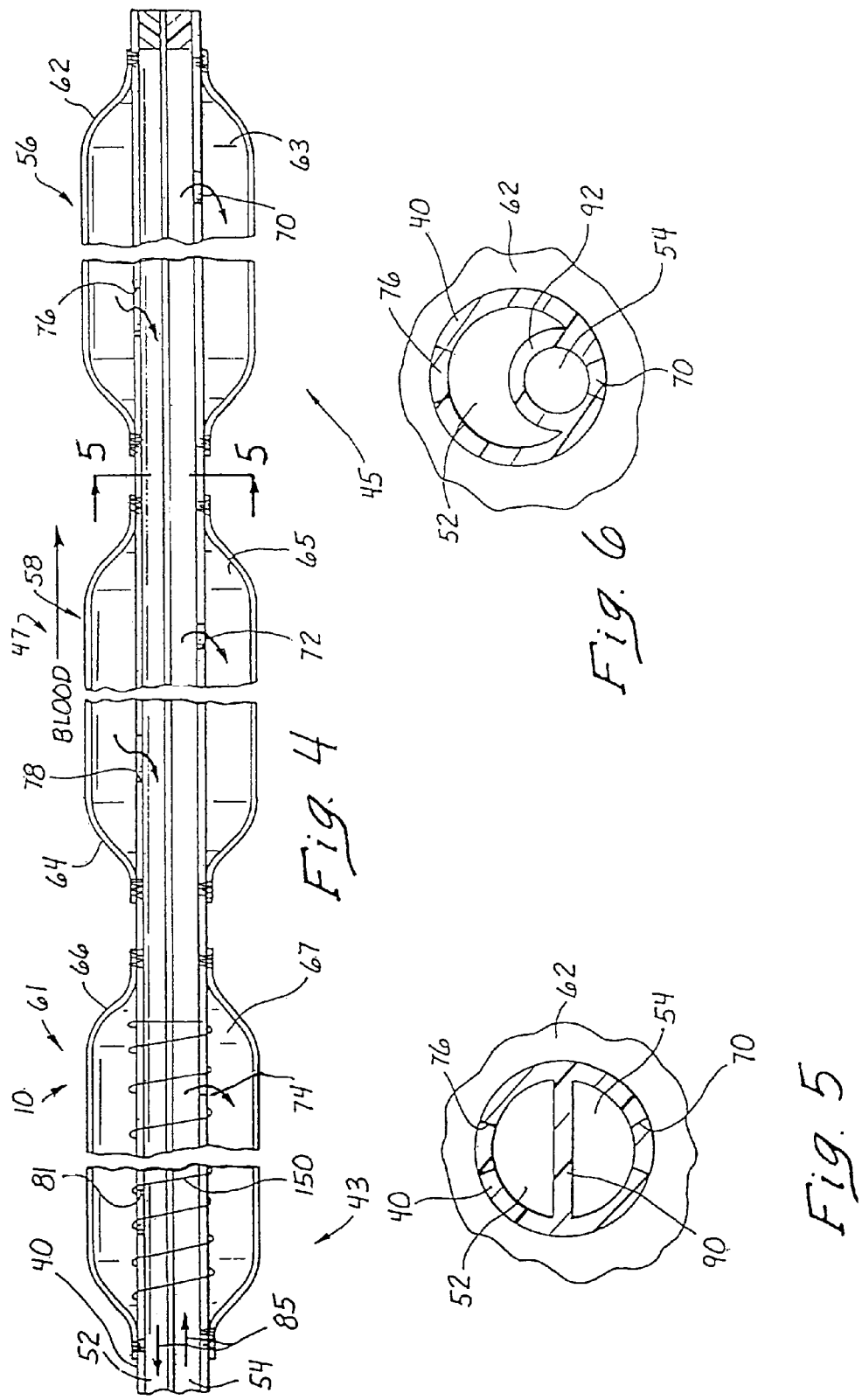

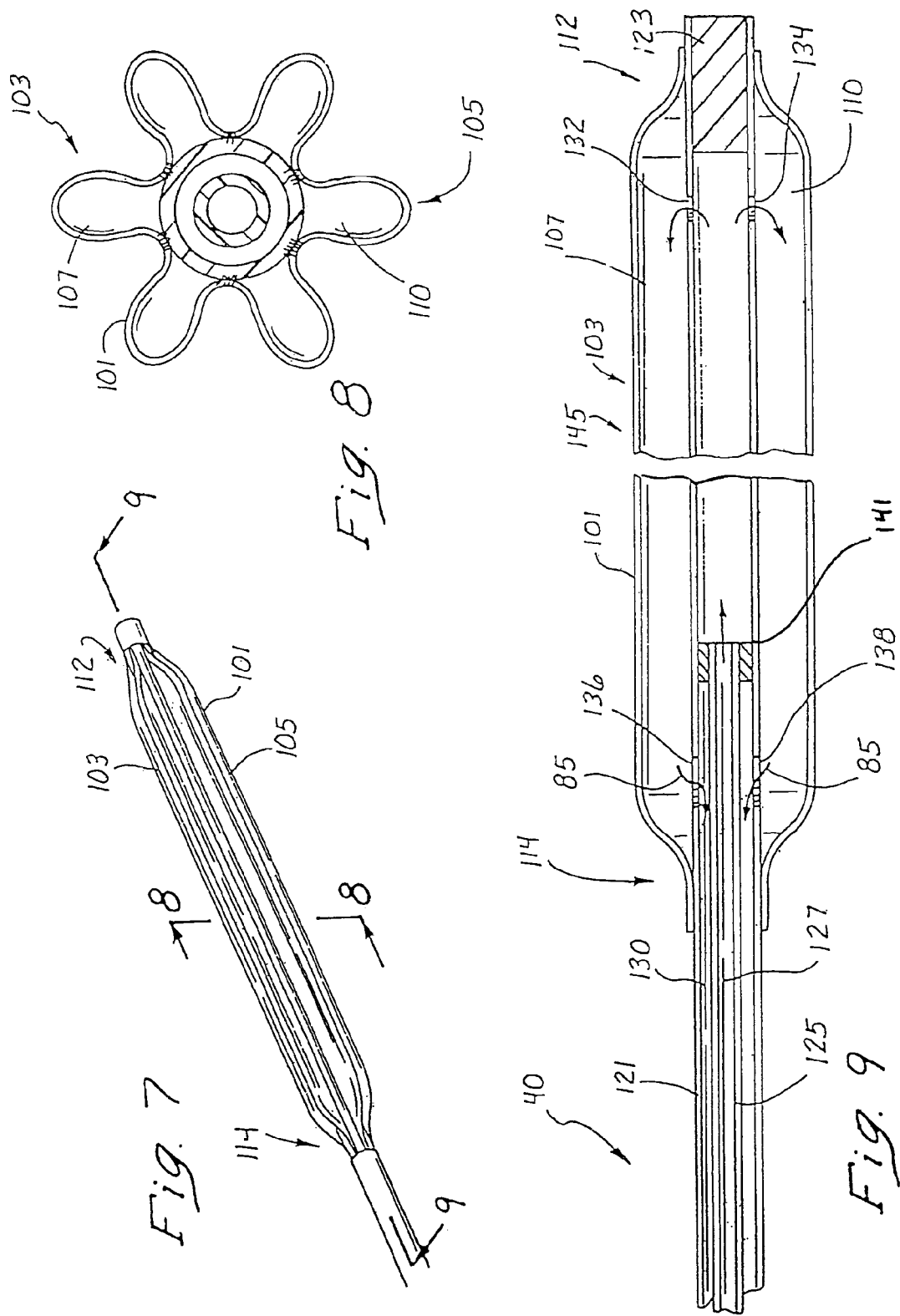

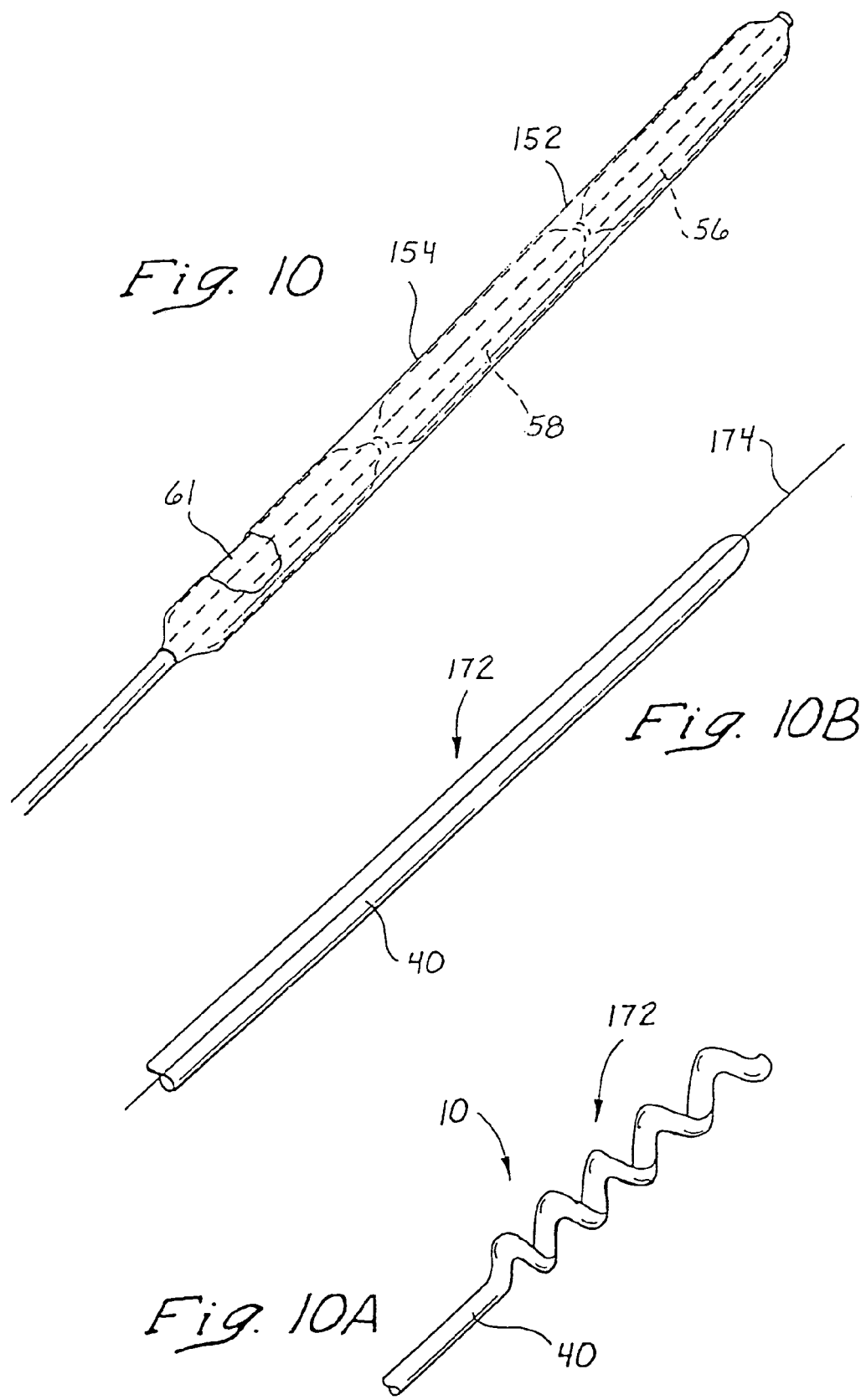

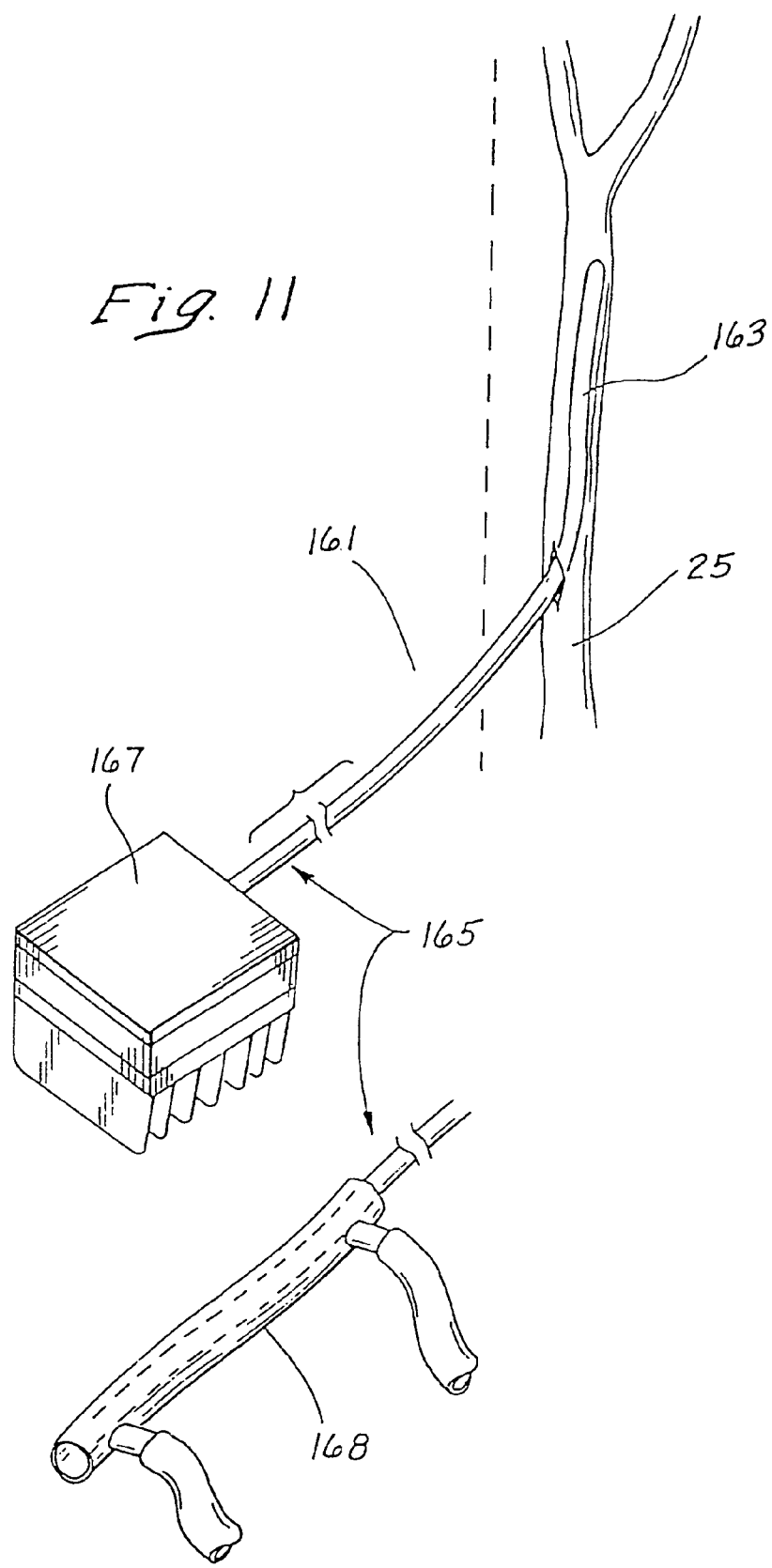

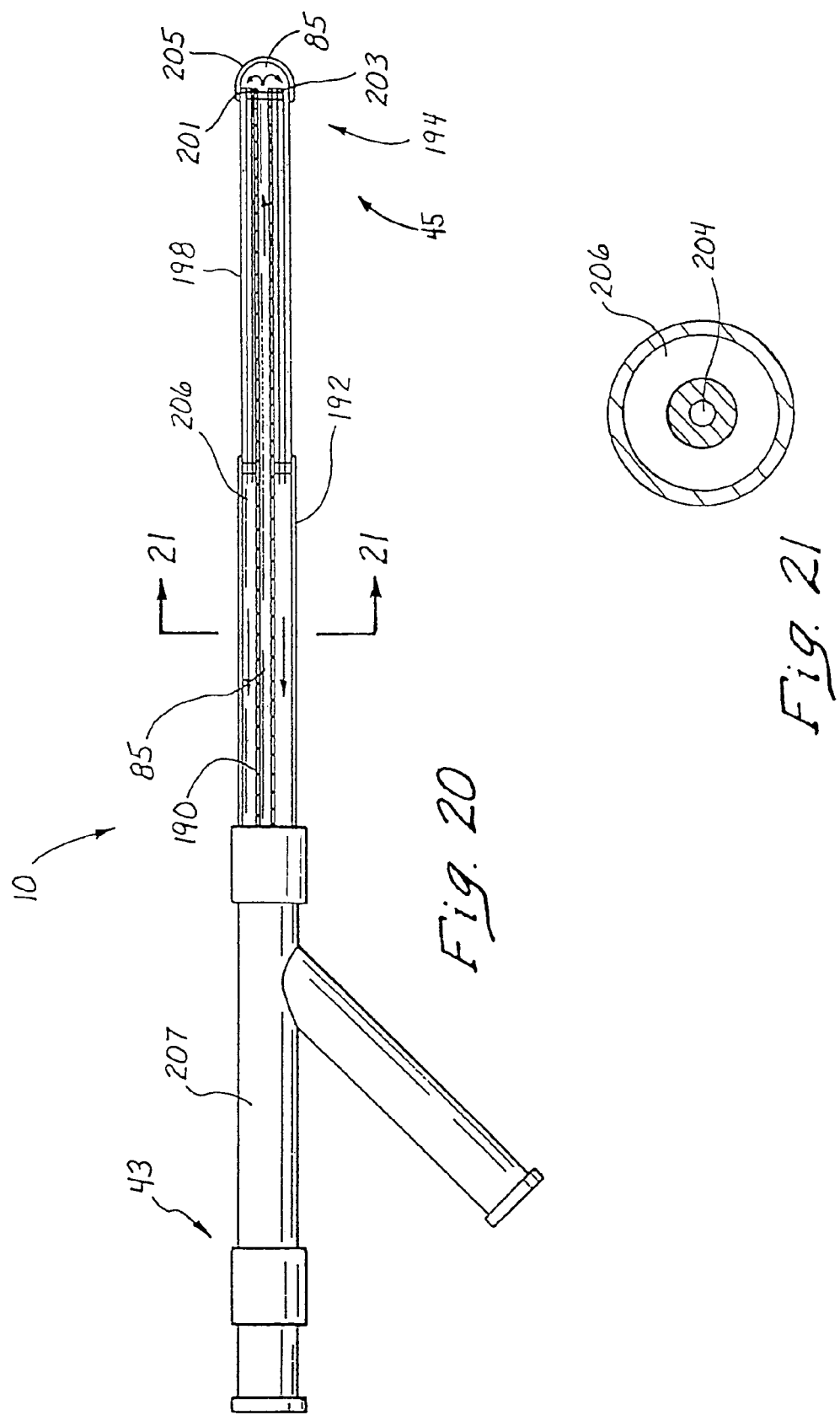

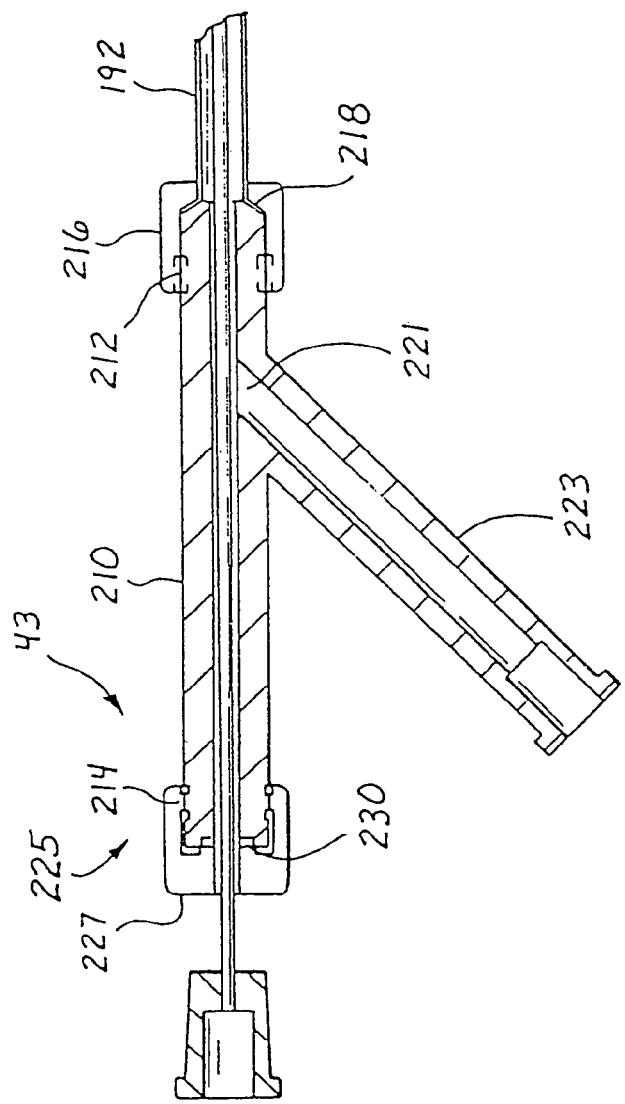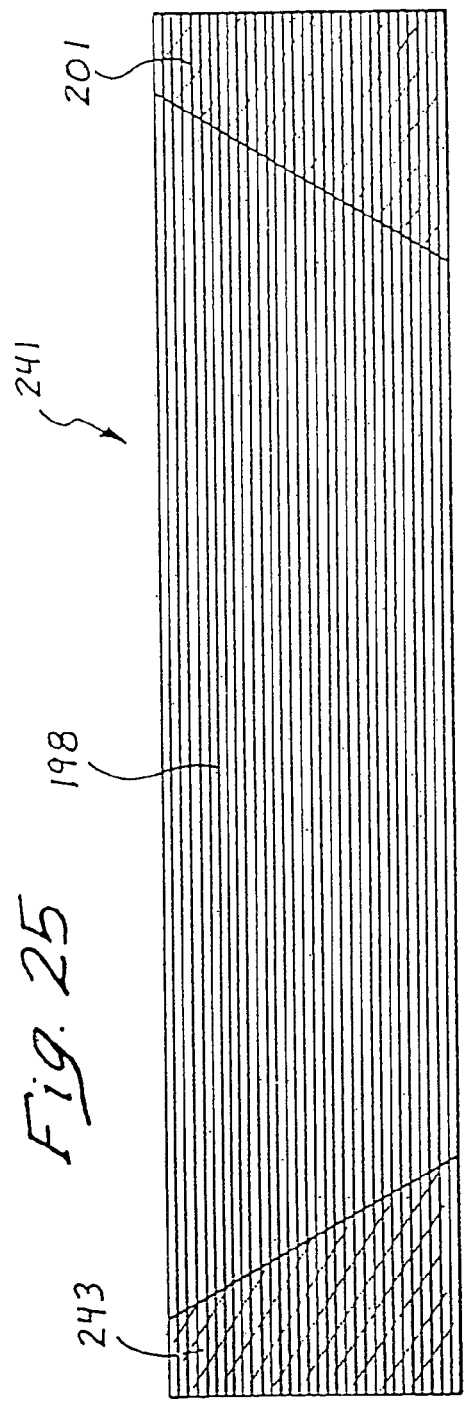

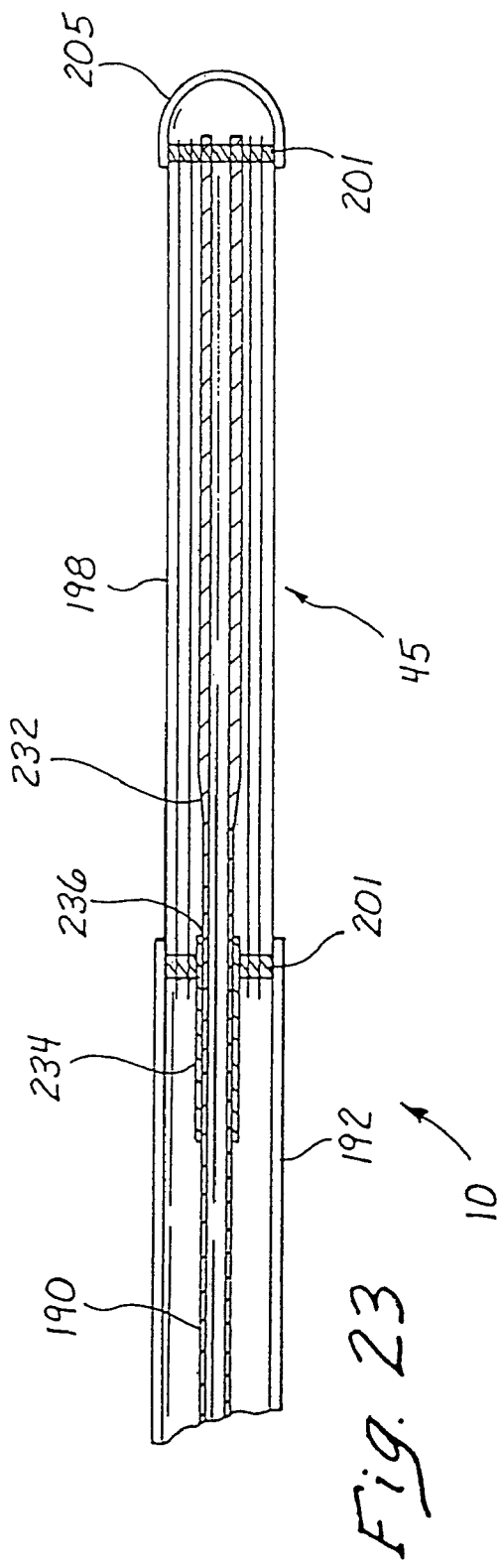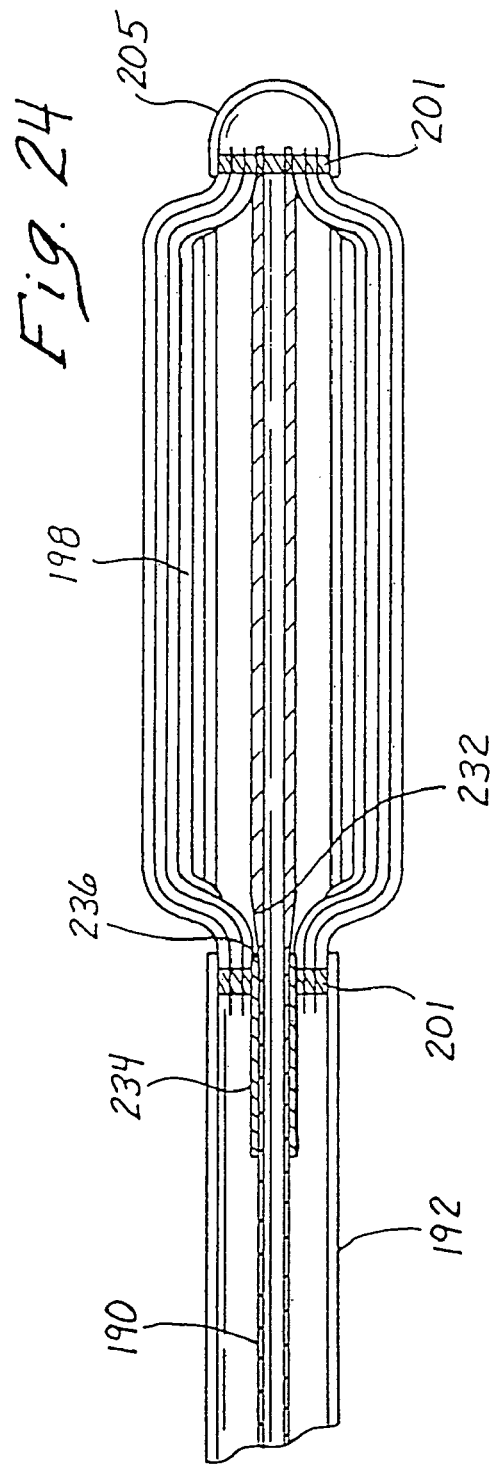

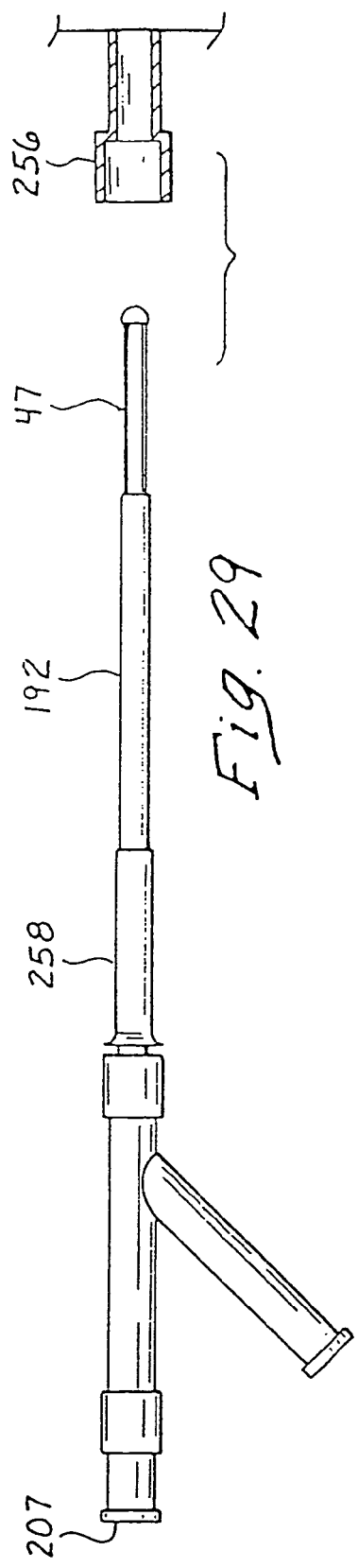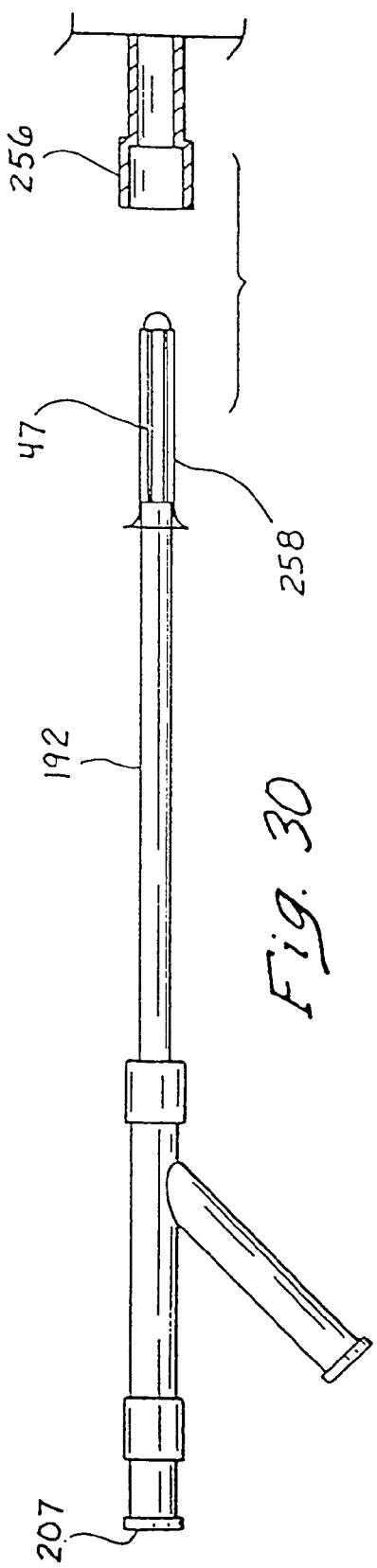

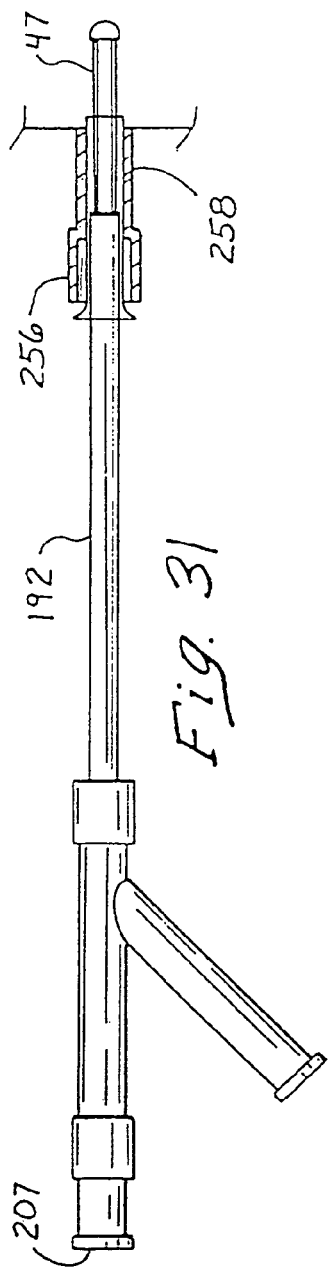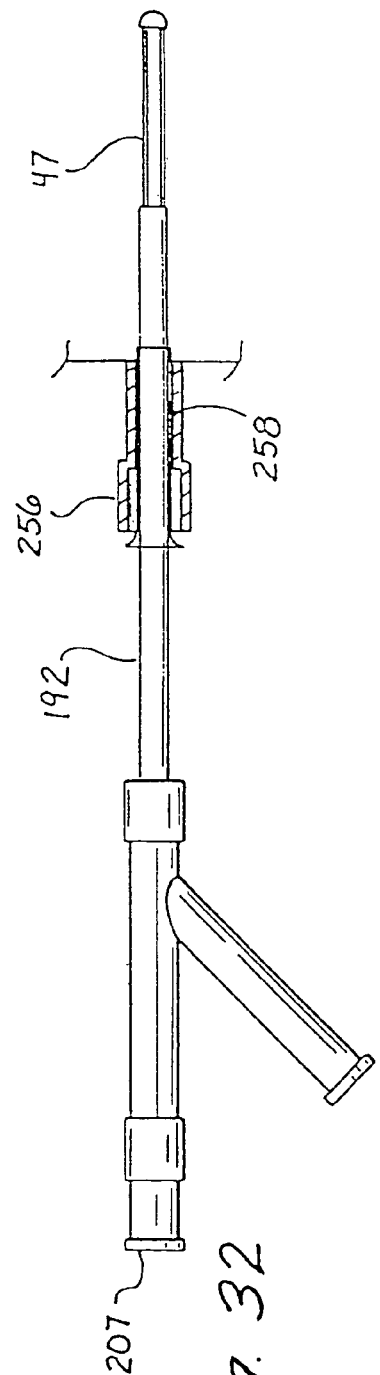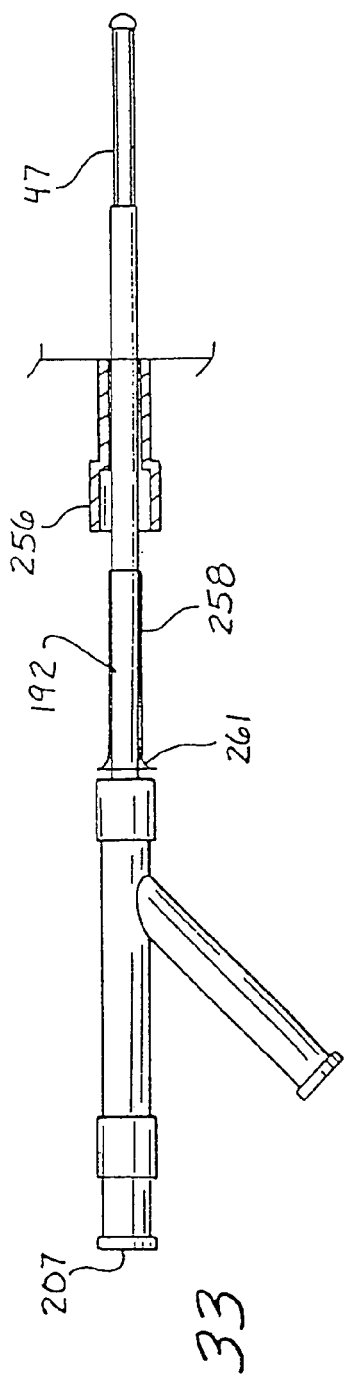

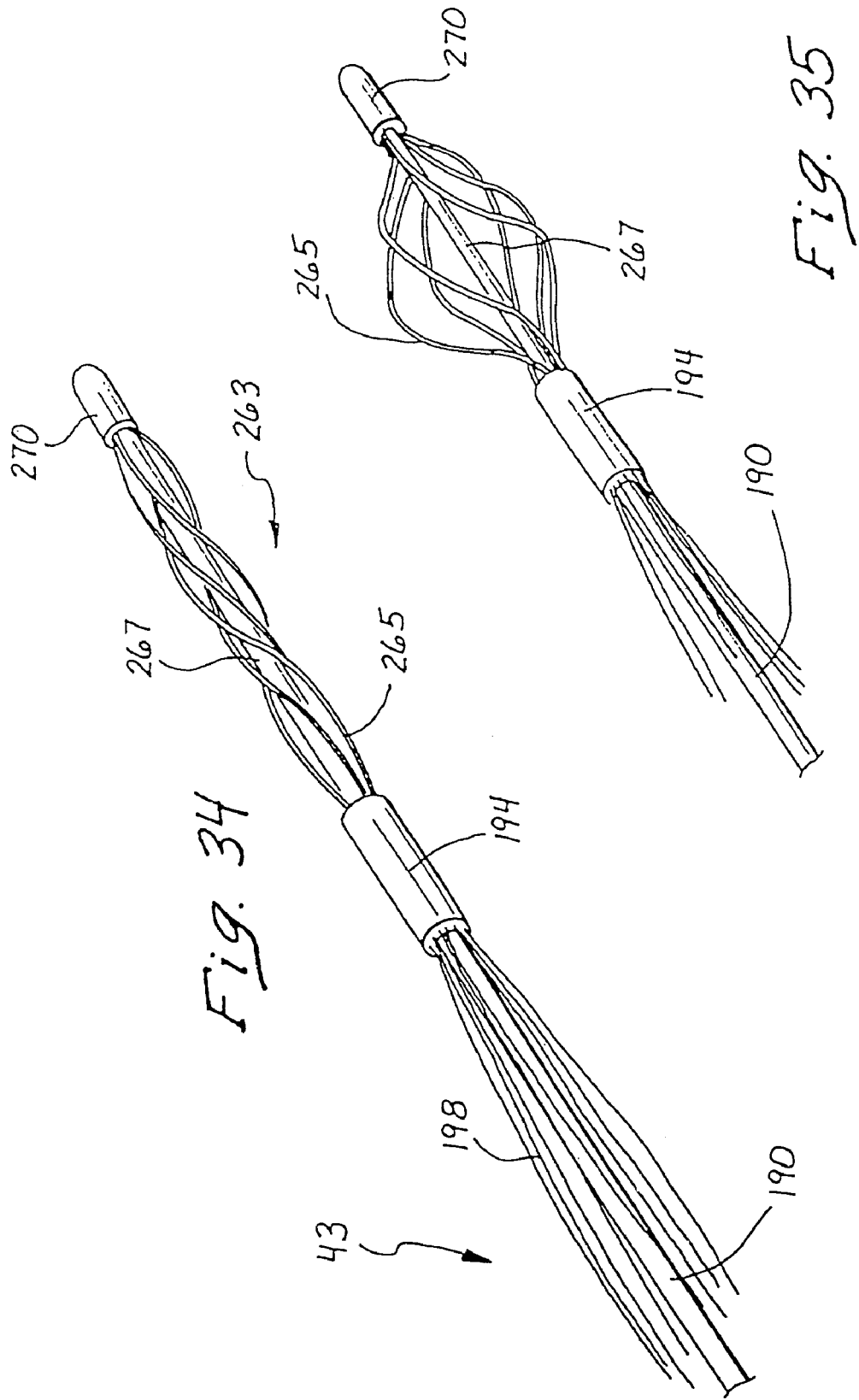

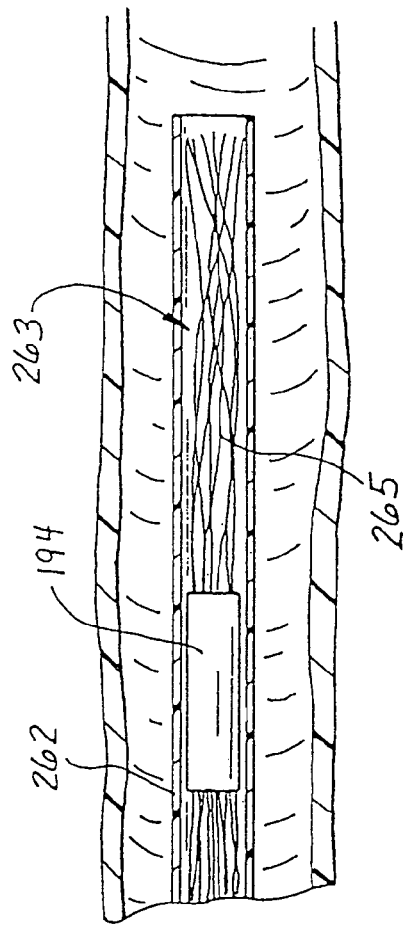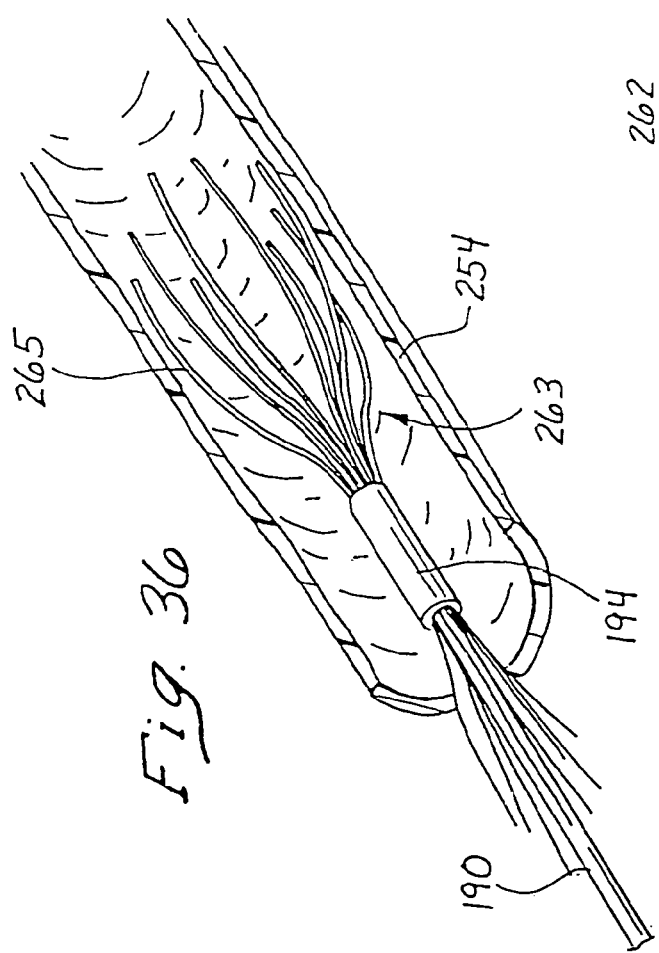

INDWELLING HEAT EXCHANGE CATHETER AND METHOD OF USING SAME

This is a continuation of U.S. patent application Ser. No. 09/946,835, filed Sep. 4, 2001, now U.S. Pat. No. 6,893,419, which is a continuation of U.S. patent application Ser. No. 09/133,813, filed Aug. 13, 1998 now U.S. Pat. No. 6,338,727, which is a continuation-in-part of U.S. patent application Ser. No. 09/063,984, filed Apr. 21, 1998, now U.S. Pat. No. 6,126,684.

BACKGROUND OF THE INVENTION

1. Field of the Invention

This invention relates generally to apparatus and methods for producing heat exchange with body tissue, and more specifically to methods and apparatus for the hypothermic treatment of a body fluid in a body conduit.

2. Discussion of the Prior Art

Many of the advantages of hypothermia are well known. By way of example, it has been found particularly desirable to lower the temperature of body tissue in order to reduce the metabolism of the body. In stroke, trauma and several other pathological conditions, hypothermia also reduces the permeability of the blood/brain barrier. It inhibits release of damaging neurotransmitters and also inhibits calcium-mediated effects. Hypothermia inhibits brain edema and lowers intracranial pressure.

In the past, hypothermic treatment has been typically addressed systemically, meaning that the overall temperature of the entire body has been lowered to achieve the advantages noted above. This has been particularly desirable in surgical applications where the reduced metabolism has made it possible to more easily accommodate lengthy operative procedures. An example of this systemic approach includes catheters for transferring heat to or from blood flowing within a patient's vessel, as disclosed by Ginsburg in U.S. Pat. No. 5,486,208. A closed loop heat exchange catheter is also disclosed by Saab in U.S. Pat. No. 5,624,392. A cooling device for whole-body hyperthermia that utilizes the circulatory system of the body is known to be more efficient since the entire volume of the body is constantly perfused with the cold fluid at a capillary level.

Likewise, various other means of cooling the body have been tried with cooling blankets, ice water bladder lavages, ice baths, esophageal catheters and their associated methods. All of these devices require a considerable time to cool the body since the primary heat transfer occurs through the skin or the skull. A more efficient body cooling device that can quickly cool and accurately control the body temperature is required.

SUMMARY OF THE INVENTION

A heat exchange catheter and method of operation are included in the present invention. The method is adapted to produce hypothermia or hyperthermia, typically in a selected portion of the body without substantially varying the temperature of the remaining portions of the body. The selected body portion will usually be associated with a body conduit which conveys a body fluid to the selected body portion. Of particular interest are the organs of the body which are commonly nourished and maintained by a flow of blood in the arterial system. For example, a flow of blood is introduced to the brain through the carotid artery. Of course the temperature of this blood is usually at the normal body temperature.

By positioning a heat exchange catheter in the body conduit, heat can be added to or removed from the body fluid to heat or cool the selected body portion. For example, the heat exchange catheter can be disposed in the carotid artery where the arterial blood flowing to the brain can be cooled. The flow of cooled blood to the brain reduces the temperature of the brain thereby resulting in cerebral hypothermia. Importantly, this temperature reduction occurs primarily and selectively in the brain; the remaining portions of the body maintain a generally normal body temperature. In accordance with this method, the selected body portion, such as the brain, can be cooled thereby providing the advantages associated with hypothermia for this body portion. The remainder of the body, such as the portions other than the brain, do not experience the reduction in temperature. Furthermore, the invention is intended to remotely alter temperature in a region other than the point of introduction into the body. This is different than devices intended for systemic temperature control.

Several factors are of interest in effecting heat transfer in a heat exchanger. These factors include, for example, the convection heat transfer coefficient of the two fluids involved in the heat exchange, as well as the thermal conductivity and thickness of the barrier between the two fluids. Other factors include the relative temperature differential between the fluids, as well as the contact area and residence time of heat transfer. The Reynolds number for each fluid stream affects boundary layers, turbulence and laminar flow.

Notwithstanding the need for localized hypothermia, there will always be those procedures which call for systemic hypothermia. Many of the advantages associated with the present invention will greatly facilitate those procedures, for example, by decreasing the number and complexity of operative steps, increasing the heat transfer capacity of the device, and addressing other concerns such as the formation of blood clots.

In one aspect of the invention a catheter is provided with an elongate configuration, a proximal end and a distal end. An outer tube having a first lumen extends between the distal end and proximal end of the catheter, and an inner tube having a second lumen is disposed within the first lumen of the outer tube. Portions of the inner tube define a first flow path extending along the second lumen, while portions of the tubes define a second flow path extending between the first tube and the second tube. A plurality of hollow fibers provide fluid communication between the first and second flow paths, and a heat exchange fluid is disposed in the hollow fibers to cool the fibers.

In another aspect of the invention, a method for making a heat exchange catheter includes the steps of providing first and second tubes having first and second lumens, respectively. A plurality of hollow fibers are connected between a first flow path extending along the second lumen and a second flow path extending along the first lumen outwardly of the second tube. The method further comprises the step of insuring that the second tube is axially or rotationally movable relative to the first tube in order to vary the configuration of the hollow fibers.

In a further aspect of the invention, a method for operating a heat exchange catheter includes the steps of inserting into a body conduit the catheter with an inner tube disposed within an outer tube and defining a first flow path interiorly of the inner tube and second flow path between the inner tube and the outer tube. This inserted catheter also includes a plurality of hollow fibers disposed in fluid communication with the first and second flow paths. The method further includes steps for creating a flow of heat exchange fluid through the first and second flow paths, and moving the inner tube relative to the outer tube to change the profile of the hollow fibers.

In a further aspect of the invention, a heat exchange catheter includes an elongate shaft with first portions defining an inlet lumen and second portions defining an outlet lumen. A first manifold is disposed in fluid communication with the inlet lumen and a second manifold disposed in fluid communication with the outlet lumen. A plurality of hollow fibers are disposed between the manifolds in fluid communication with the inlet and outlet lumens. The catheter is adapted to receive a heat exchange fluid and to direct the heat exchange fluid through the hollow fibers to exchange heat through the hollow fibers.

In still a further aspect of the invention, a catheter is adapted to exchange heat with the body fluid flowing in a first direction through a body conduit. The catheter includes a shaft having an input lumen and an output lumen. A plurality of hollow fibers define a heat exchange region and collectively define an output surface of the heat exchange region. The input lumen of the shaft is coupled to the hollow fibers at a first location while the output lumen of the shaft is coupled to the hollow fibers at a second location disposed in the first direction from the first location.

Another aspect of the invention includes a method for exchanging heat with a body fluid in a body conduit. In this case, a catheter is provided with a plurality of hollow heat exchange fibers extending in fluid communication with an inlet lumen and an outlet lumen of the catheter. The heat exchange fibers collectively define a first cavity in heat transfer relationship with a body fluid in a body conduit.

In an additional aspect of the invention, an operative area of the catheter is sized and configured for disposition in a vessel containing blood. The operative area is adapted to perform a predetermined function, and the blood in the vessel has a tendency to form clots. In this aspect of the invention, the catheter is provided with a snare disposed relative to the operative area and being operable from a proximal end of the catheter to move from a low-profile state facilitating insertion of the catheter, to a high-profile state facilitating the capture of blood clots.

In still a further aspect of the invention, a heat exchange catheter is adapted for cooling the blood of a patient. The catheter includes a heat exchange region with a plurality of fibers each having a hollow configuration. A heat exchange fluid is disposed in the hollow fibers to cool the fibers and a coating is disposed on the outer surface of the fibers to inhibit formation of blood clots.

These and other features and advantages of the invention will be better understood with a description of the preferred embodiments of the invention and reference to the associated drawings.

DESCRIPTION OF THE DRAWINGS

FIG. 1 is side elevation view of a patient lying in a prone position with a heat exchange catheter of the present invention appropriately inserted to facilitate hypothermic treatment of the patient's brain;

FIG. 4 is an enlarged axial cross section view of a plurality of balloons disposed in the heat exchange region of the catheter;

FIG. 5 is a radial cross section view of the catheter taken along lines 5-5 of FIG. 4;

FIG. 6 is a radial cross section view similar to FIG. 5 of a further embodiment of the catheter;

FIG. 7 is a perspective view of a further embodiment of the catheter wherein multiple balloons are provided with a longitudinal configuration;

FIG. 8 is a radial cross section view taken along lines 8-8 of FIG. 7;

FIG. 9 is an axial cross section view taken along lines 9-9 of FIG. 7;

FIG. 10 is a perspective view of the catheter illustrated in FIG. 3 further illustrating structures which can facilitate mixing and heat exchange;

FIG. 10A is a perspective view of an embodiment of the catheter having a distal end with a pigtail configuration;

FIG. 10B is a perspective view of the catheter illustrated in FIG. 10A with the distal end straightened by a stylet 174 to facilitate insertion of the catheter;

FIG. 11 is a schematic view of an embodiment including a heat pipe;

FIG. 12 is a schematic view, partially in section, of a heat pipe adapted for use in the embodiment of FIG. 11;

FIG. 20 is a side elevation view partially in section and illustrating a further embodiment of the catheter of the present invention;

FIG. 21 is a radial cross-section view taken along the lines 21-21 of FIG. 20;

FIG. 22 is an axial cross-section view of the proximal end of the catheter illustrated in FIG. 20;

FIG. 23 is an axial cross-section view of the distal end of a further embodiment illustrating the heat exchange region in a low-profile state;

FIG. 24 is an axial cross-section view similar to FIG. 23 and illustrating the heat exchange region in a high-profile state;

FIGS. 25-27 illustrate a preferred method for manufacturing the heat exchange region of a hollow fiber embodiment of the cavity;

FIG. 25 is a top plan view of a mat formed of the heat exchange fibers;

FIG. 26 is a perspective view illustrating formation of the mat around the distal ends of the concentric tubes;

FIG. 27 is a side elevation view illustrating attachment of the mat assembly to an outer tube of the catheter;

FIG. 29-33 illustrate a method for introducing the catheter of the present invention;

FIG. 29 is a side elevation view illustrating a introducing sheath in a first position removed from the heat exchange region;

FIG. 30 is a side elevation view illustrating the sheath in a second position over the heat exchange region of the catheter;

FIG. 31 is a side elevation view illustrating the catheter and sheath being inserted into an introducer;

FIG. 32 is a side elevation view illustrating the catheter further inserted with the sheath maintained in the introducer;

FIG. 33 is a side elevation view illustrating removal of the sheath to the first position;

FIG. 34 is a perspective view of a further embodiment of the catheter including a distal clot filter in a low-profile state;

FIG. 35 is a perspective view illustrating the catheter of FIG. 34 with the clot filter in a high-profile state;

FIG. 36 is a perspective view of a catheter with a clot filter having free ends and automatically deployable to a high-profile state; and FIG. 37 is a side elevation view of the catheter of FIG. 36 with a sheath maintaining the clot filter in a low-profile state.

DESCRIPTION OF THE PREFERRED EMBODIMENTS AND BEST MODE OF THE INVENTION

Figure 2:
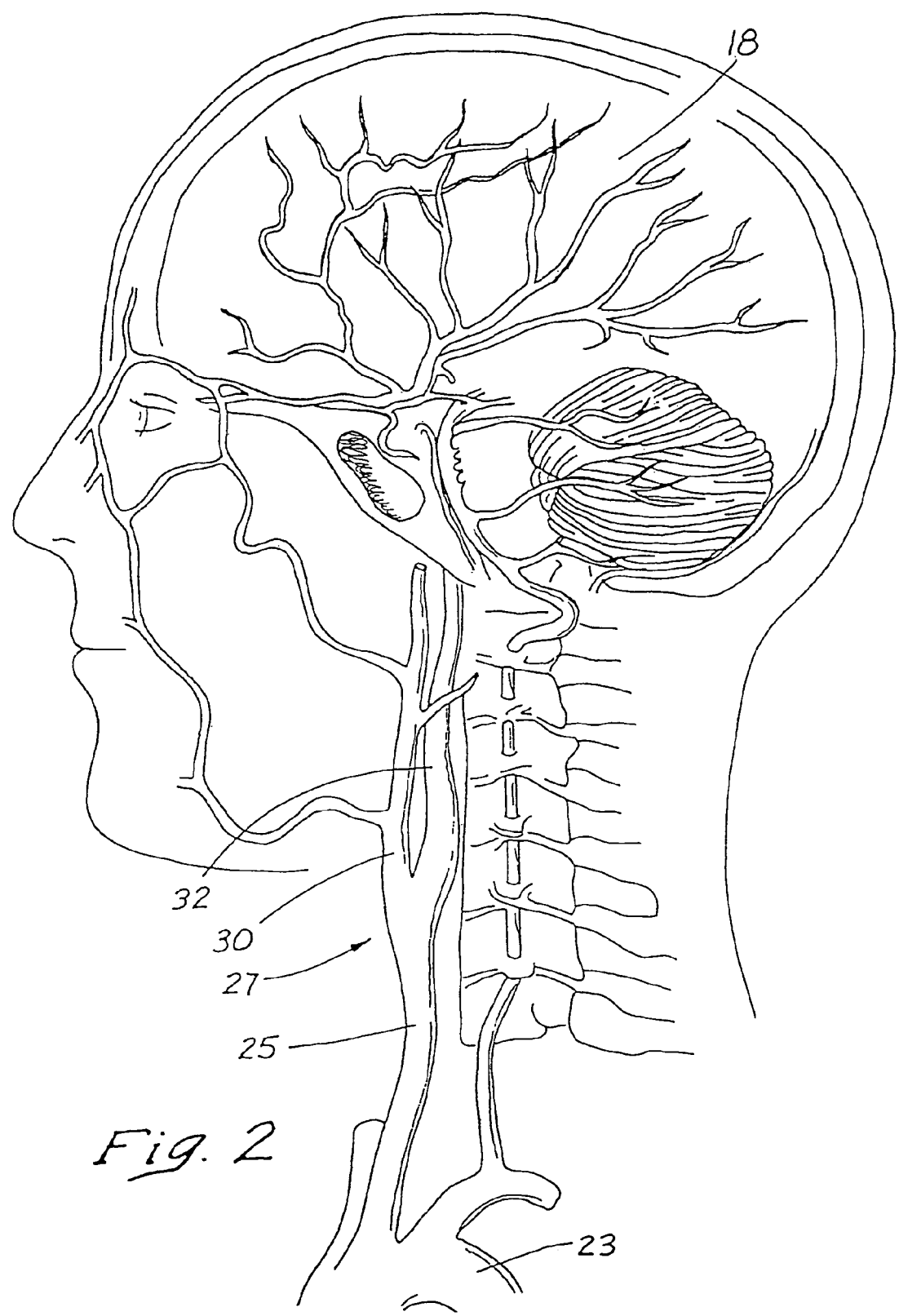
FIG. 2 is an enlarged side elevation view showing the vasculature associated with the patient's head and brain.

A heat exchange catheter is illustrated in FIG. 1 and designated generally by the reference numeral 10. The catheter 10 is operatively disposed with respect to a body 12 of a patient having a groin 14, a head 16, and a brain 18. More specifically, the catheter 10 can be inserted percutaneously through a puncture or surgical cut down at the groin 14, and into the femoral artery 21. Following this initial introduction, the catheter 10 can be moved through the femoral artery 21 and the aortic arch 23, into the common carotid artery 25 best illustrated in FIG. 2. This common carotid artery 25 divides at a carotid branch 27 into an external carotid artery 30, which primarily supplies blood 31 to the face of the patient, and an internal carotid artery 32, which primarily supplies blood to the brain 18 of the patient.

In the concept of this invention, the brain 1S is merely representative of a portion of the body 12 of the patient, and the arteries 21, 25, 30 and 32 are merely representative of conduits which supply a body fluid, such as blood, to a selected portion of the body 12, such as the brain 18. By cooling the body fluid, such as blood 31, in the body conduit, such as the artery 32, the specific body portion, such as the brain 18, can be selectively cooled without significantly affecting the temperature of the remaining portions of the body 12.

Selective hypothermic treatment of the brain 18 is initially of particular interest as it captures the advantages of hypothermia during operative procedures associated with the brain 18 without also capturing the disadvantages of hypothermia with respect to other areas of the body 12. Thus, a surgeon operating to treat an aneurysm in the brain 18, for example, can initially cool the brain 18 in order to facilitate that procedure. This selective hypothermia will be particularly appreciated in those surgical procedures which are primarily directed to the brain 18. Procedures such as stroke, trauma, and other brain related injuries will also benefit up to and during from this selective hypothermia treatment.

Figure 3:
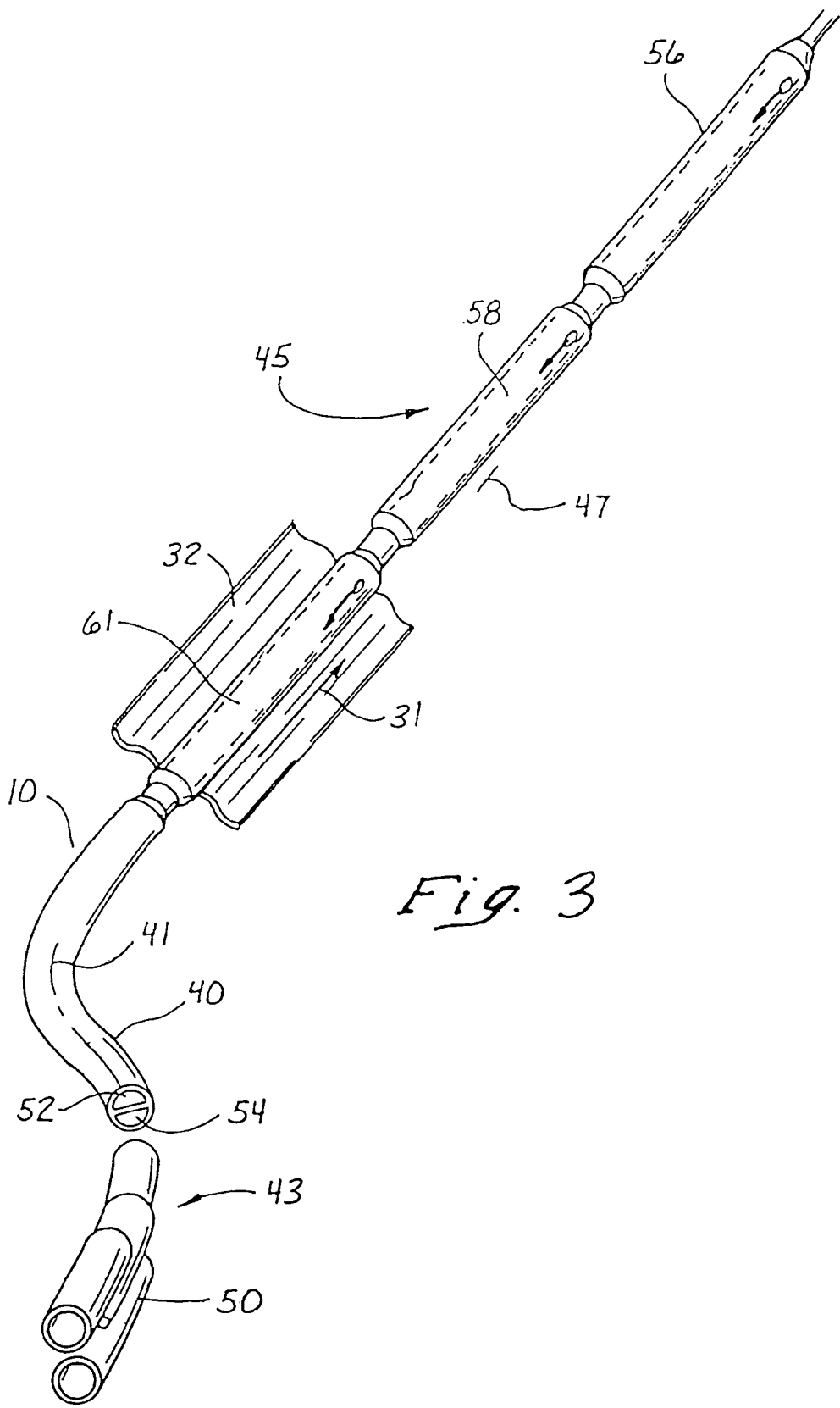
FIG. 3 is a perspective view partially in section of a heat exchange region of the catheter.

A preferred embodiment of the catheter 10 of the present invention is illustrated in FIGS. 3 and 4. From this perspective view, it can be seen that the catheter 10 includes a shaft 40 having an axis 41 which extends between a proximal end 43 and a distal end 45. When operatively disposed, a heat exchange region 47 at the distal end 45 is operatively disposed within the body 12, and a hub 50 at the proximal end 43 is disposed outside of the body 12. Within the shaft 40, a plurality of lumens 52 and 54 extend in fluid communication with the hub 50 and the heat exchange region 47.

A preferred embodiment of the heat exchange region 47 is illustrated in greater detail in FIG. 4 where three balloons 56, 58 and 61 are individually, separately and axially disposed along the shaft 40. It will be appreciated that although the illustrated embodiment includes three balloons, a single balloon or double balloon embodiment may offer further advantages in a particular procedure. All of the balloons 56, 58 and 61 are illustrated to have a significantly larger diameter than the shaft 40. This may not be the case in other embodiments. More specifically, it may be desirable to maximize the dimension of the shaft 40 in order to facilitate flow of the heat exchange fluid. This will also minimize the volume of fluid in the balloon and promote a more rapid heat exchange. In one such embodiment, the diameter of the shaft 40 is in a range between 50 and 90 percent of the diameter of the balloons 56, 58 and 61.

Each of the balloons 56, 58 and 61 can be formed from a piece of sheet material 62, 64 and 66 which is bound or otherwise fixed to the shaft 40 to form a cavity 63, 65 and 67, respectively. An inlet hole 70 provides fluid communication between the lumen 54 and the cavity 63 of the balloon 56. Similar inlet holes 72 and 74 are provided for the balloons 58 and 61. In a like manner, an outlet hole 76 can be formed in the wall of the shaft 40 to provide fluid communication between the lumen 52 and the cavity 63 of the balloon 56. Similar outlet holes 78 and 81 are provided for the balloons 58 and 61, respectively. With this structure, it can be seen that the lumen 54 functions primarily as an inlet lumen for a heat exchange fluid which is illustrated generally as a series of arrows designated by the reference numeral 85.

Initially, the heat exchange fluid 85 is introduced through the hub 50 (FIG. 3) and into the inlet lumen 54. From the lumen 54, the heat exchange fluid 85 passes through the inlet holes 70, 72, 74 and into the respective balloon cavity 63, 65 and 67. The heat exchange fluid 85 then passes into the outlet hole 76, 78, 81 and into the outlet lumen 52 and the hub 50 to regions exterior of the catheter 10.

After the heat exchange fluid 85 is remotely cooled, it is circulated through the balloon cavities 63, 65 and 67 to provide a cold temperature fluid on the inner surface of the sheet materials 62, 64 and 66 which form the walls of the balloons 56, 58 and 61, respectively. With a body fluid, such as blood 31, flowing exteriorly of the balloons 56, 68 and 61, heat transfer occurs across the sheet materials 62, 64 and 66, respectively.

It can be appreciated that this circulation of the heat exchange fluid 85 can be formed with any structure of the shaft 40 which provides two lumens, such as the lumens 52 and 54, each of which can have access to the balloon cavities, such as the cavities 63, 65 and 67. In one embodiment of the shaft 40 illustrated in FIG. 5, a septum 90 is provided which separates the cylindrical shaft 40 into two equally sized lumens 52 and 54. In the embodiment of FIG. 6, the cylindrical shaft 40 is provided with a cylindrical septum 92 which provides the lumen 54 with a circular cross section and the lumen 52 with a moon-shaped cross section. In such an embodiment, the lumen 54 must be defined off-axis from the shaft 40 in order to have access to the balloon cavities, such as the cavity 63.

One of the advantages of a multiple balloon embodiment of the catheter 10 is that the flow and temperature of the heat exchange fluid 85 can be more easily controlled along the entire length of the heat exchange region 47. Realizing that the heat exchange fluid 85 will be coolest prior to entering into a heat exchange with the blood 31, and warmest after that heat exchange, one can advantageously control not only the velocity and volume of flow, but also the direction of flow within each discrete balloons 56, 58 and 61. Another advantage of a multiple balloon design is the ability of the catheter to bend and flex when placed in a curved vasculature. Single balloon designs would be rigid, stiff and inflexible by comparison.

In order to facilitate the maximum heat exchange between the fluid 85 and the blood, it is desirable to provide a balanced flow of the heat exchange fluid 85 along the entire length of the heat exchange region 47. In the embodiment illustrated in FIG. 4, efficient heat transfer is facilitated by countercurrent flow where the heat exchange fluid 85 is directed to flow counter to the flow of the blood 31. To that end, the inlet holes 70, 72 and 74 are positioned distally of the outlet holes 76, 78 and 81, respectively. As the blood 31 flows distally along the outer surface of the catheter 10, this relative position of the inlet holes and outlet holes causes the heat exchange fluid to flow in the opposite direction, proximally in each of the balloons 56, 58 and 61.

The amount of flow within each of the balloons 56, 58 and 61 can also be controlled by the size of the inlet holes 70, 72, 74 and outlet holes 76, 78 and 81. In a preferred embodiment, this flow control is provided solely by the inlet holes 70, 72 and 74; the outlet holes 76, 78 and 81 are sized larger than their respective inlet holes so that they offer little resistance to flow. In this embodiment, the inlet holes 70, 72 and 74 are sized to be progressively smaller from the distal end 45 to the proximal end 43. Thus the hole 70 is larger than the hole 72 which is larger than the hole 74. As a result, the resistance to the flow of heat exchange fluid 85 in the most distal balloon 56 is less than that in the most proximal balloon 61. This ensures that the coolest heat exchange fluid 85 is shared equally among all of the balloons 56, 58 and 61 regardless of their position along the shaft 40. In an embodiment wherein the flow is controlled by the outlet holes 76, 78 and 81, these holes can also be provided with a relatively reduced size from the distal end 45 to the proximal end 43. With any of these structures, a more balanced flow of the heat exchange fluid can be achieved in order to facilitate the highest degree of heat exchange along the entire heat exchange region 47. Alternatively, the flow of heat exchange fluid can also be balanced by providing the holes 76, 78 and 81 with non-circular configurations. For example, these holes may be formed as longitudinal slits extending axially of the catheter.

A further embodiment of the invention is illustrated in FIG. 7 wherein a single sheet of material 101 is used to form separate and distinct individual balloons, two of which are designated by the reference numerals 103 and 105. As opposed to the radial balloons 56, 58 and 61 of the previous embodiment, the balloons 103 and 105 extend axially along the surface of the shaft 40. For example, the balloons 103 and 105 form individual balloon cavities 107 and 110, respectively, which extend from a distal end 112 to a proximal end 114.

This embodiment of the catheter containing the axial balloons 103 and 105 may include a shaft 40 with a slightly different configuration. As best illustrated in FIG. 9, the shaft 40 may include an outer tube 121 having an outer surface to which the sheet material 101 is attached and within which is disposed a distal sealing plug 123. An inner tube 125, which can be disposed coaxially with the outer tube 121, has an inner lumen 127 and defines with the outer tube 121 an outer lumen 130. A pair of inlet holes 132 and 134 provide flow fluid communication between the inner lumen 127 and the balloon cavities 107 and 110, respectively. Similarly, a pair of outlet holes 136 and 138 provide fluid communication between the balloon cavities 107 and 110 and the outer lumen 130, respectively. An inner plug 141 disposed between the inner tube 125 and outer tube 121 to seal the outer lumen 130 between the inlet holes 132, 134 and outlet holes 136, 138. For the reasons previously noted, a preferred embodiment has inlet holes 132, 134 which are disposed distally of and sized smaller than the outlet holes 136, 138, respectively. This orientation will provide countercurrent flow in a catheter 10 which is inserted downstream into an artery such as the carotid artery 25.

Embodiments which are intended to maximize heat transfer will take advantage of the fact that heat exchange is enhanced when either, or both, the body fluid or the heat exchange fluid is provided with well mixed flow. Mixing can be enhanced by providing irregular surfaces next to which either of these fluids flow. For example, with reference to FIG. 4, it will be noted that a spring 150 can be disposed around the shaft 40 inside each of the balloons, such as the balloon 61. In this embodiment, the spring 150 upsets the laminar flow of the heat exchange fluid 85 thereby producing the desired mixing of this fluid. Other structures can be positioned within the cavities formed by the balloons 56, 58 and 61.

Mixing can also be enhanced within the body fluid which flows along the outer surface of the catheter 10. In this case, the multiple radial balloon embodiment illustrated in FIG. 4 is of advantage as each of the balloons 56, 58 and 61 represents a peak and defines with the adjacent balloon a valley along which the blood 31 flows. This series of peaks and valleys also upsets the laminar flow of the body fluid. Mixing of the body fluid can also be enhanced by providing other structures along the outer surface of the sheet material 62, 64 and 66 which form the balloons as well as any exposed areas of the shaft 40 in the heat exchange region 47. By way of example, a multiplicity of granules 145 can be adhered to the outer surface of the radial balloons 56, 58 and 61 or the axial balloons 103 and 105 as illustrated in FIG. 9. Ridges can also be provided along these surfaces.

With some body fluids, it may be desirable to inhibit turbulent flow and facilitate laminar flow. This may be true for example in the case of blood where undesirable hemolysis may occur in response to increased turbulence. Such an embodiment might be particularly desirable for use with radial balloons where an outer balloon 152 would promote laminar flow by reducing the height differential between the peaks and valleys defined by the balloons 56, 58 and 61. This outer balloon 152 is best illustrated in FIG. 10. To further promote laminar flow, the outer surface of any structure in the heat exchange region 47 can be provided with a coating 154, such as a hydrophilic or a hydrophobic coating to modify the boundary layer. Thus the outer surface of the shaft 40 as well as the outer surface of any of the balloons 56, 58, 61, 103, 105 and 152 can be provided with the coating 154. The coating 154 may also include other ingredients providing the catheter 10 with additional advantageous properties. For example, the coating 154 may include an antithrombogenic ingredient such as heparin or aspirin. Such a coating 154 would not only inhibit platelet deposition but also the formation of blood clots.

As previously noted, the characteristics of the heat exchange fluid 85 may also be of importance in a particular heat exchange environment. Although the heat exchange fluid 85 may include various liquids, it is believed that gases may provide the greatest temperature differential with the body fluid. Particularly if this fluid includes blood, gases that are inert or otherwise compatible with the vascular system will be appreciated. Although several inert gases might fulfill these requirements, carbon dioxide is used for the heat exchange fluid 85 in a preferred embodiment of the invention.

A further embodiment of the catheter 10 is contemplated for maximizing the surface area available for heat exchange. As illustrated in FIGS. 10A and 10B, the catheter 10 can be formed with a distal end 45 of the shaft 40 disposed in the natural configuration of a spiral or pigtail 172. The relatively large diameter of the pigtail 172 facilitates heat exchange, but tends to deter from a low profile desire for insertion. Under these circumstances, it may be advantageous to insert the catheter 10 over a stylet or guidewire 174 in order to straighten the pigtail 172 as illustrated in FIG. 10B.

Hyperthermia and hypothermia for selective regions of the body can also be achieved by placing in the body conduit, such as the carotid artery 25, a heat pipe 161 best illustrated in the schematic view of FIG. 11. In this embodiment, the heat pipe 161 includes a distal end 163 and proximal end 165. The distal end 163 is adapted to be placed within the body conduit, such as the carotid artery 25. The proximal end 165 of the heat pipe 161 is adapted to be connected to an external heat sink or cooler, such as a thermoelectric cooler 167 or water jacket 168. A wick structure 170 is provided in the heat pipe 161 to facilitate a flow of heat exchange fluid from the cooler 167 to the distal end 163.

In a process involving the heat pipe 161, illustrated in FIG. 12, the heat exchange fluid is moved from the proximal end 165 of the heat pipe 161 either by gravity or by capillary action of the wick structure 170 to the distal end 163. At the distal end 163 of the heat pipe 161, heat is transferred from the body fluid, such as blood, to the heat exchange fluid in its liquid state. This heat exchange liquid absorbs a heat of vaporization as it passes into a vapor state in the heat pipe 161. The heat exchange fluid in its vapor state creates a pressure gradient between the ends 163 and 165 of the heat pipe 161. This pressure gradient causes the vapor to flow to the cooler 165 where it is condensed giving up its latent heat of vaporization. The heat exchange fluid in its liquid state then passes back through the heat pipe 161 through the wick structure 170 or by gravity. The passive heat exchange system provided by the heat pipe 161 is vacuum-tight and can be operated with a minimum amount of the heat exchange fluid.

Figure 13:
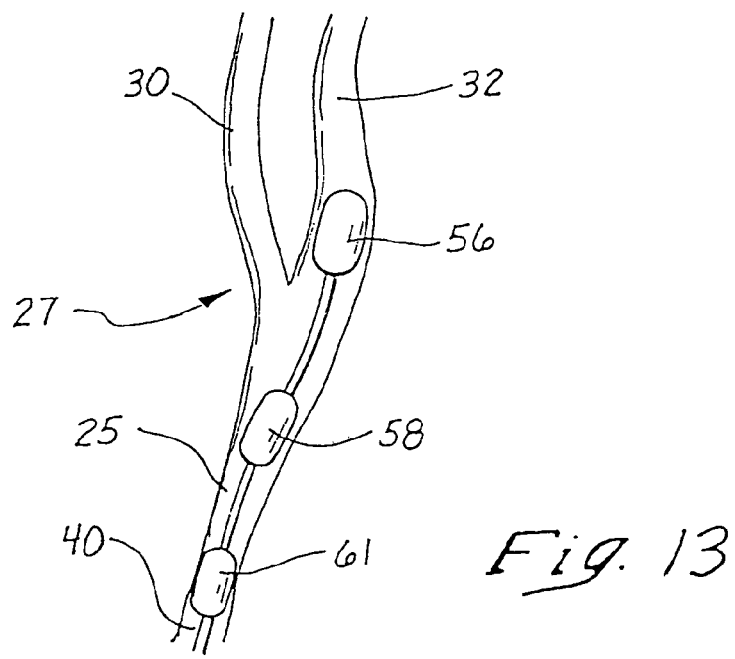
FIG. 13 is a top plan view of carotid artery branch illustrating one method of operation associated with the catheter.

Although the heat exchange catheter 10 will be advantageous in the hyperthermic or hypothermic treatment of any portion of the body 12, it is believed that it will be particularly appreciated in those procedures which can benefit from the hypothermic treatment of the brain 18, such as the treatment of ischemic stroke and/or head-trauma. As previously noted in comments directed to FIG. 1, the catheter 10 can be inserted into the femoral artery in the groin 14 and directed through the aortic arch 23 into the common carotid artery 25. As illustrated in FIG. 13, the catheter 10 can then be moved into the region of the arterial branch 27 where it will encounter the external carotid artery 30 and the internal carotid artery 32. Since the external carotid artery 30 is directed primarily to the facial regions, it does not supply a significant amount of blood to the brain 18. In contrast, the internal carotid artery 32 is almost solely responsible for feeding the capillary bed of the brain 18. Based on these considerations, hypothermic treatment of the brain 18 is best addressed by cooling the blood in the internal carotid artery 32 without wasting any of the cooling properties on the external carotid artery 30. In a method associated with one embodiment of the invention, the most distal of the balloons, such as the balloon 56 in FIG. 13 is preferably positioned within the internal carotid artery 32. The more proximal balloons 58 and 61 can be disposed along the common carotid artery 25. This embodiment of the catheter 10 and its associated method will achieve a higher degree of heat transfer within the internal artery 32 than the external artery 30.

Figure 14:
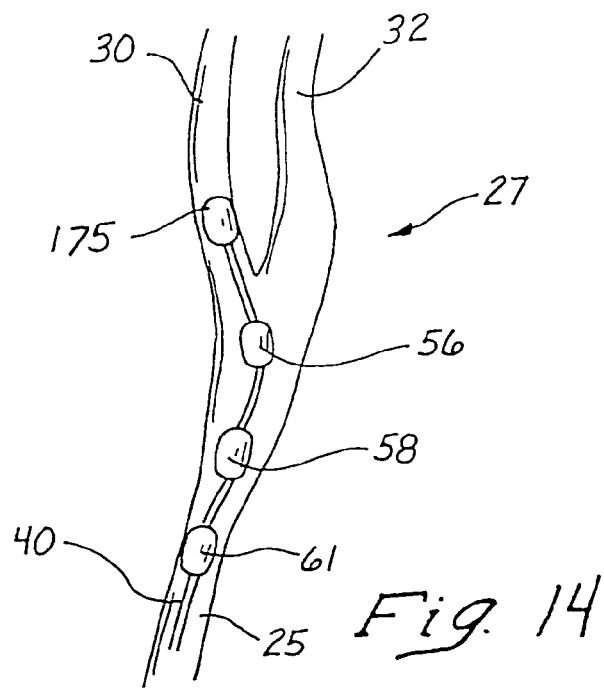
FIG. 14 is a top plan view similar to FIG. 13 and showing a further method of operation with the catheter.

In another embodiment of the catheter 10 best illustrated in FIG. 14, an occlusion balloon 175 is provided distally of the heat exchange region 47. In this embodiment, the occlusion balloon 175 will preferably be inflatable through a separate lumen in the shaft 40. As the catheter 10, approaches the carotid branch 27, the occlusion balloon 175 is directed into the external carotid artery 30 and inflated in order to at least partially occlude that artery. The remaining proximal balloons 56, 58 and 61 in the heat exchange region 47 are left within the common carotid artery 25 to promote heat exchange with the blood flowing to the branch 27. With the external artery 30 at least partially occluded, heat transfer occurs primarily with the blood flowing into the internal carotid artery 32.

Figures 15, 16:
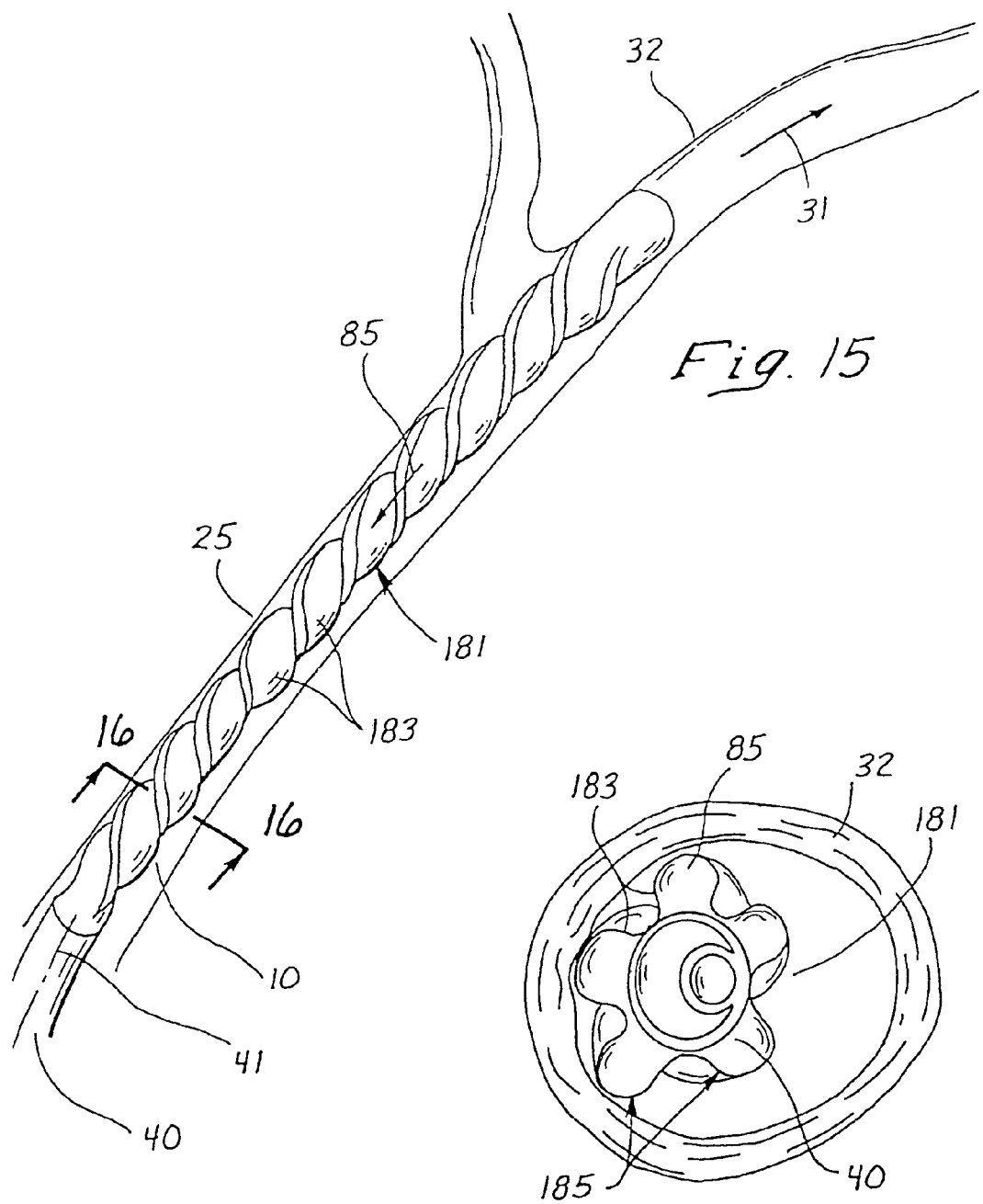
FIG. 15 is a top plan view of the carotid branch similar to FIG. 13 and showing a further method of operating a heat exchange catheter.
FIG. 16 is a radial cross section of the catheter taken along lines 16-16 of FIG. 15.

A further embodiment of the invention is illustrated in FIG. 15 operatively disposed in the common carotid artery 25 and internal carotid artery 32. In this case, the catheter 10 includes a balloon 181 which is attached to the distal end of the shaft 40 and provided with a spiral configuration. More specifically, the balloon 181 may be formed from several individual balloons, as with the embodiment of FIG. 7, for as individual flutes 183 on the single balloon 181. In either case, the separate balloons (such as the balloons 103, 105 of FIG. 7) or the flutes 183 are oriented in a spiral configuration around the axis 41 of the catheter 10. The shaft 40 can be provided with any of the configurations previously discussed such as the eccentric configuration of FIG. 6.

By providing the balloon 181 with a spiral configuration, heat exchange is enhanced by at least two of the factors previously discussed. Notably, the surface area of contact is increased between the blood 31 flowing externally of the balloon 181 and the heat exchange fluid flowing internally of the balloon 181. The spiral configuration also enhances the mixing properties of both the blood 31 and the heat exchange fluid 85.

As noted, the heat exchange fluid 85 may be cooled to a sub-zero temperature. In order to thermally protect the internal lining of the artery 32 from direct contact with the sub-zero coolant, it may be desirable to provide the tips of the flutes 183 with a thicker wall 185, as shown in FIG. 16. This thicker wall 185 might be advantageous in any of the balloon configurations previously discussed, but would appear to be most advantageous in the embodiments of FIGS. 7 and 15 where the contact with the artery 32 tends to be more localized by the longitudinal balloons 103, 105 (FIG. 7) on the spiral flutes 183 (FIG. 15).

Figure 17:
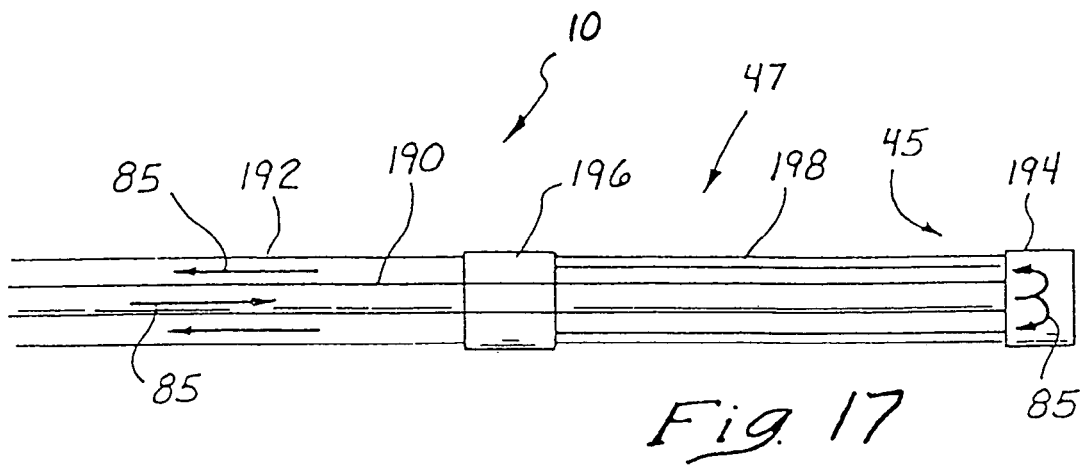
FIG. 17 is an axial cross section view of a further embodiment of the invention including hollow fibers in the heat exchange region.

Still a further embodiment of the invention is illustrated in FIG. 17. In this embodiment, the shaft 40 includes an inner tube 190 disposed within an outer tube 192. These tubes 190, 192 may be concentric and longitudingly movable relative to each other. The tubes 190, 192 terminate respectively in manifolds 194, 196. Between these manifolds 194, 196, a multiplicity of hollow fibers 198 can be disposed at the distal end 45 to define the heat exchange region 47 of the catheter 10. The hollow fibers 198 each include an internal lumen which provides fluid communication between the manifolds 194 and 196. In operation, the heat exchange fluid 85 flows distally along the inner tube 190 into the distal manifold 194. From this manifold 194, the heat exchange fluid 85 flows into the internal lumens of the hollow fibers 198 proximally to the proximal manifold 196. The warmer heat exchange fluid 85 flows proximally from the manifold 196 between the inner tube 190 and outer tube 192.

Preferably, the hollow fibers 193 have a wall thickness that is thin enough to allow maximum heat transfer, yet strong enough to withstand the pressure requirements of the heat exchange fluid 85. The hollow fibers 198 are further adapted to achieve ideal heat transfer by the maximization of both surface area and coolant flow. The smaller the diameter of the fibers 198, the more fibers can be fit into the catheter 10 with a corresponding increase in surface area. As the diameter of the fibers 198 is decreased, however, the resistance to fluid flow increases thus lowering the coolant flow rate. The effect of the inflow and outflow lumens must also be considered in determining the fluid resistance. Ideally, the wall thickness of the hollow fibers 198 is in a range between 0.00025 inches and 0.003 inches. In a preferred embodiment the wall thickness is in a range between 0.00075 inches and 0.002 inches, and ideally 0.00125 inches. The outer diameter of the hollow fibers 198 will typically be between 0.008 inches and 0.035 inches. In a preferred embodiment the outer diameter is in a range between 0.010 inches and 0.018 inches, and ideally 0.015 inches.

It will be noted that the heat exchange fluid 85 flowing, in the inner tube 190 is insulated in several respects from the blood stream outside the catheter 10. This flow channel in the inner tube 190 is insulated not only by the wall of the outer tube 192, but also by the coolant returning in the flow channel associated with the outer tube 192. The heat exchange fluid 85 in the inner tube is further insulated by the thickness of the inner tube wall.

In the heat exchange region 47, the wall thicknesses associated with the inner tube 190 and the outer tube 192 is preferably reduced in order to provide additional volume for the hollow fibers 198. With a reduced wall thickness, the inner tube 190 also contributes to the heat exchange occurring in the region 47.

The hollow fibers 198 offer several advantages to this embodiment of the catheter 10. Notably, they provide a very high surface area between the blood 31 and the heat exchange fluid 85. This greatly enhances the heat exchange characteristics of this embodiment. Countercurrent flow can also be maintained further facilitating the heat exchange capabilities of this catheter.

Figure 18:
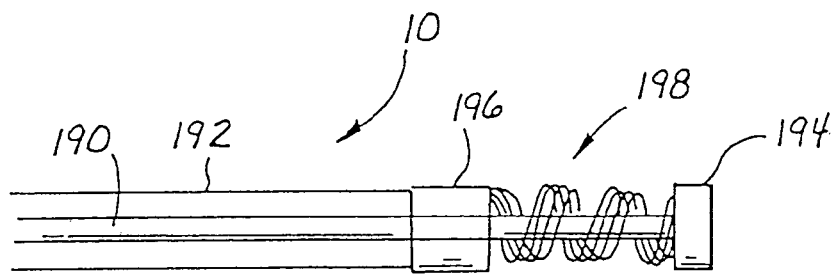
FIG. 18 is a side elevation view similar to FIG. 17 and illustrating the hollow fibers in a compacted configuration.
Figure 19:
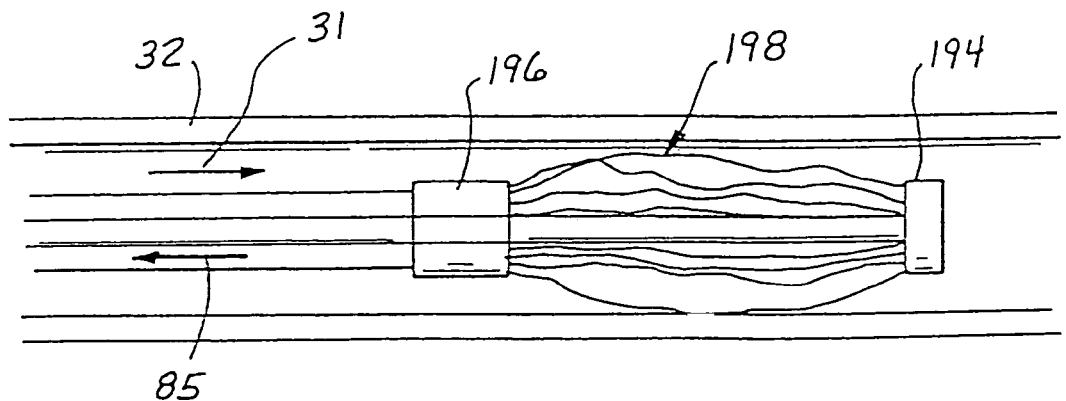
FIG. 19 is an axial cross section view of the catheter of FIG. 17 operatively disposed and configured to permit the hollow fibers to float and undulate within a blood stream.

The hollow fibers 198 can be spiraled as illustrated in FIG. 18 by twisting the inner tube 190 with respect to the outer tube 192. This characteristic can be used to provide a shorter and lower profile heat exchange region 47 in order to facilitate introduction of the catheter 10. A lower profile may also be obtained by separating the manifolds 194 and 196 a distance substantially equal to the length of the fibers 198. This will tend to hold the fibers in a straight, parallel relationship and thereby facilitate introduction of the catheter 10. The spiraled configuration of the hollow fibers 198 can be maintained during heat exchange in order to further increase the heat exchange area per unit length of the catheter 10. Alternatively, the fibers 198 can be positioned to loosely float and undulate between the manifolds 194 and 196 as illustrated in FIG. 19. This characteristic of the fibers 198 will not only provide the increased heat exchange area desired, but also promote mixing within the blood 31.

The fibers 198 will typically be formed of common materials such as polyolefin nylon and polyurethane. The fibers can be coated with a clot-inhibiting material such as heparin. Other materials advantageous for inhibiting the formation of blood clots might include those which form polymer surfaces with 16 or 18 carbon alkyl chains. These materials attract albumin and thereby inhibit clot formation. In a further embodiment, the fibers 193 can be provided with micropores which permit the leaching of such clot inhibiting pharmaceuticals as heparinized saline which could also serve as the heat exchange fluid 85.

The embodiment of FIG. 20 also takes advantage of the significant heat exchange characteristics associated with the hollow fibers 198. In this embodiment, the manifold 194 at the distal end 45 of the catheter 10 includes a potting seal 201 with a distal surface 203. The fibers 198 are held in the potting seal 201 with the lumens of the fibers 198 exposed at the surface 203. The distal end of the inner tube 190 is also held in the potting seal 201 with its lumen exposed at the distal surface 203. In this embodiment, the manifold 194 includes a cap 205 which may have a hemisphere configuration. This cap extends over the distal surface 203 of the potting seal 201 and provides fluid communication between the lumen of the inner tube 190 and the lumens of the hollow fibers 198. This cap 205 may also be constructed of materials and wall thicknesses that insulate the blood vessels from potential contact with a cold catheter tip.

FIG. 21 illustrates in a cross-sectional view a first flow channel 204 which extends along the lumen of the inner tube 190 and a second flow channel 206 which extends along the lumen of the outer tube 192 outwardly of the inner tube 190. As the heat exchange fluid 85 is introduced into the first flow channel 204, its direction is reversed in cap 205 so that the flow of the fluid 85 in the hollow fibers is counter to the flow of the body fluid, such as blood, in the body conduit, such as the artery 32. After moving through the fibers 198, the heat exchange fluid 85 passes along the second flow channel 206 between the inner tube 190 and outer tube 192, and exits the catheter 10 at the proximal end 43.

The embodiment of FIG. 20 also includes a Y-connector 207 disposed at the proximal end 43 of the catheter 10. This connector 207 is shown in greater detail in the enlarged view of FIG. 22. In this view it can be seen that the connector 207 includes a body 210 with screw threads 212 at its distal end and screw threads 214 at its proximal end. At the distal end of the body 210, a screw cap 216 mates with the screw threads 212 to engage an annular flange 218 at the proximal end of the outer tube 192. In this manner, the Y-connector 207 forms a seal with the proximal end of the outer tube 192 and provides fluid communication between the second flow channel 206 and a lumen 221 of the Y-connector 207. A side port 223 communicates with this lumen 221 and provides an exit port for the secondary flow channel 206.

In order to prevent leakage from the lumen 221 at the proximal end 43 of the Y-connector 207, a releasable seal 225 can be formed at the proximal end of the body 210. In the illustrated embodiment, the releasable seal 225 includes a cap 227 which is threaded to register with the threads 214 of the body 210. This cap 227 extends around the proximal end of the body 210 and compresses an elastomeric washer 230 against the body 210 and the outer surface of the inner tube 190. By tightening the cap 227, the washer 230 is compressed to seal the lumen 221. This compression also functions to inhibit, but not necessarily prevent, axial movement between the outer tube 192 and inner tube 190. The releasability of the seal 225 can be appreciated in order to facilitate this relative movement between the tubes 190 and 192 for the reasons previously discussed. This form of a releasable seal 225 is commonly referred to as a Tuohy-Borst seal.

The relative movement between the inner and outer tubes 190 and 192, respectively, will be appreciated in order to provide the tubes 190 and 192 with a first position wherein the fibers 198 have a low profile configuration as illustrated in FIG. 23. The relative movement will also be appreciated in order to provide the tubes 190 and 192 with a second position wherein the hollow fibers 198 form an increased profile as illustrated in FIG. 24. It can be appreciated that this profile will facilitate heat exchange by providing an increased spacing of the individual hollow fibers in the body fluid.

Another feature associated with these two positions is illustrated in FIG. 23 where the inner tube 190 is expanded in thickness at its distal end in order to form a ramp or taper 232. In this embodiment, the taper 232 is annular and extends radially outward with progressive distal positions along the tube 190. As the inner tube 190 is drawn proximally relative to the outer tube 192, the taper 232 is brought into sealing engagement with the proximal end of the hollow fibers 198 and potting seal 201. This effectively seals the distal end of the outer tube 192 against the outer surface of inner tube 190, and prohibits any loss of the heat exchange fluid 85 between the inner and outer tubes 190 and 192 at the distal end 45.

This loss of the heat exchange fluid 85 can also be addressed with a seal tube 234 which can be positioned between the inner and outer tubes 190, 192 and inwardly of the hollow fibers 198. In this embodiment, a distal end 236 of the seal tube 234 is generally coextensive with the distal end of the outer tube 192. The seal tube 234 is preferably provided with an inner diameter greater than the outer diameter of the inner tube 190. As a result, the inner tube 190 is free to move relative to the outer tube 192 to achieve the advantages previously discussed. However, when the inner tube 190 is drawn sufficiently proximal of the outer tube 192, the taper 232 will contact the distal end 236 of the seal tube 234. This effectively forms the seal between the inner and outer tubes 190 and 192, respectively at the distal end of the outer tube 192. With the taper 232 wedged against the seal tube 234, the fibers 198 are maintained in their operative free-floating configuration as illustrated in FIG. 24.

Alternatively, a non-tapered inner tube 190, can be mated with a closely fitted seal tube 234. With very small and controlled differences between the outside diameter of the inner tube 190 and the inside diameter of the seal tube 234, for example 0.0005 to 0.003 inches, an effective seal can be constructed without the taper 232. This embodiment relies on the length of the seal tube 234, the surface tension of the coolant fluid 85, and the small capillary gap to create a resistance greater than the pressure of the coolant fluid during operation. This design does not require the inner tube to be moved a fixed distance relative to the outer tube and does not require a constant tension between the inner and outer tubes to effect a seal.

The seal tube 234 is preferably constructed of polyimide which allows for a precision and constant inner diameter. In addition, polyimide is available in very thin wall thicknesses so that the seal tube 234 will not occupy a significant portion of the annular space which is more appropriately dedicated to the fibers 198.

Figure 26:
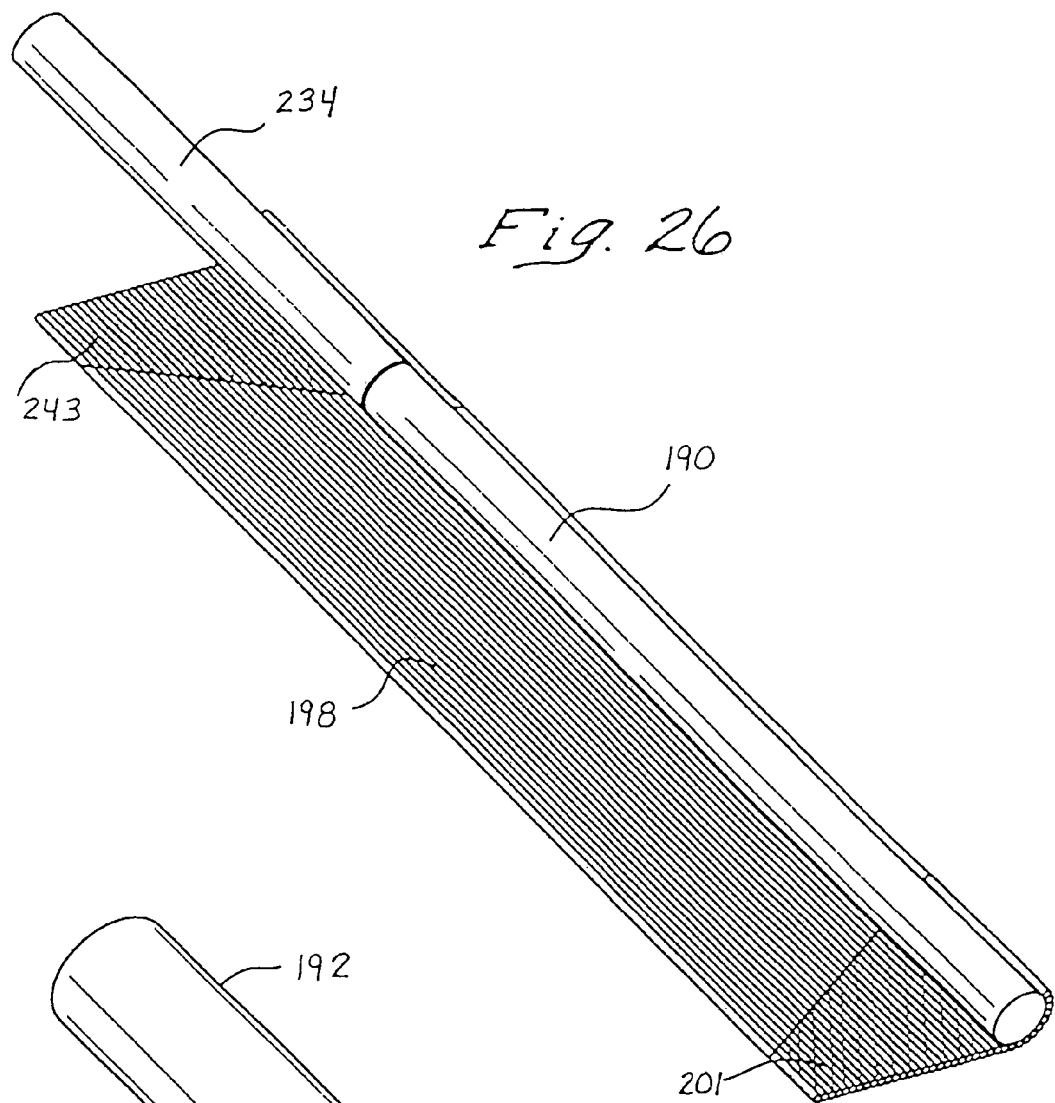
Figure 27:
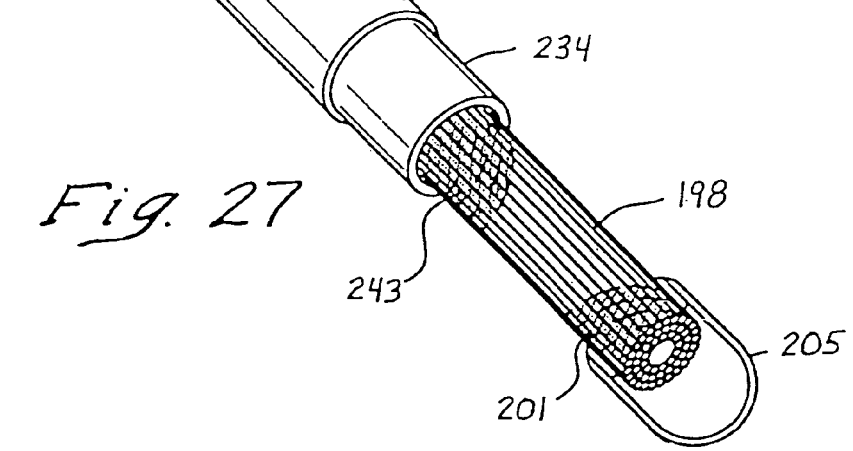

A method for manufacturing the hollow fiber embodiments of the catheter 10 is illustrated in FIGS. 25-27. In FIG. 25, a planar mat 241 of the hollow fibers 198 is formed with a generally planar configuration. In this mat 241, the fibers 198 are oriented in a generally parallel configuration with angled potting seals 201 and 243 formed at opposite ends of the fibers 198. This fiber mat 241 can be rolled onto the outer surfaces of the inner tube 190 and seal tube 234 as illustrated in FIG. 26. In this step, the potting seal 201 is formed around the distal end of the inner tube 190 while the potting seal 243 is formed around the distal end of the seal tube 234.

By initially forming the fibers 198 into the mat 241, a generally uniform thickness of the mat 241 can be maintained. Rolling the mat 241 onto the tubes 190 and 234 maintains this uniform thickness and also facilitates orientation of the fibers 198 onto the cylindrical tubes 190 and 234. This technique also forms an inwardly spiraling helical bond joint profile that aids in directing the blood flow in order to inhibit clot formation by preventing stagnant blood flow areas at the bond joint. With the potting seals 201 and 243 suitably bonded to the tubes 190 and 234, respectively, the cap 205 can be mounted over the distal end of the fibers 198 as previously discussed. At the proximal end of the fibers 198, the seal tube 234 can be mounted in the distal end of the outer tube 192 as illustrated in FIG. 27.

The seal tube 234 offers some interesting possibilities for the infusion of fluids at the distal end 45 of the catheter 10. Of course, it is always possible to provide an additional lumen within the shaft of the catheter 10. In such an embodiment, the fluid to be infused could be injected into the additional lumen at the proximal end 43 to exit the catheter at the distal end 45. Alternatively, the fluid to be infused might be included in the heat exchange fluid 85. The tolerance between the seal tube 234 and the outer diameter of the inner tube 190 could then be controlled to provide a calibrated leak of the heat exchange fluid 85 at the distal end 45 of the catheter 10. Micro holes might also be drilled into the outer tube 192 or inner tube 190 to provide for a controlled leakage of the infusion fluid.

Figure 28:
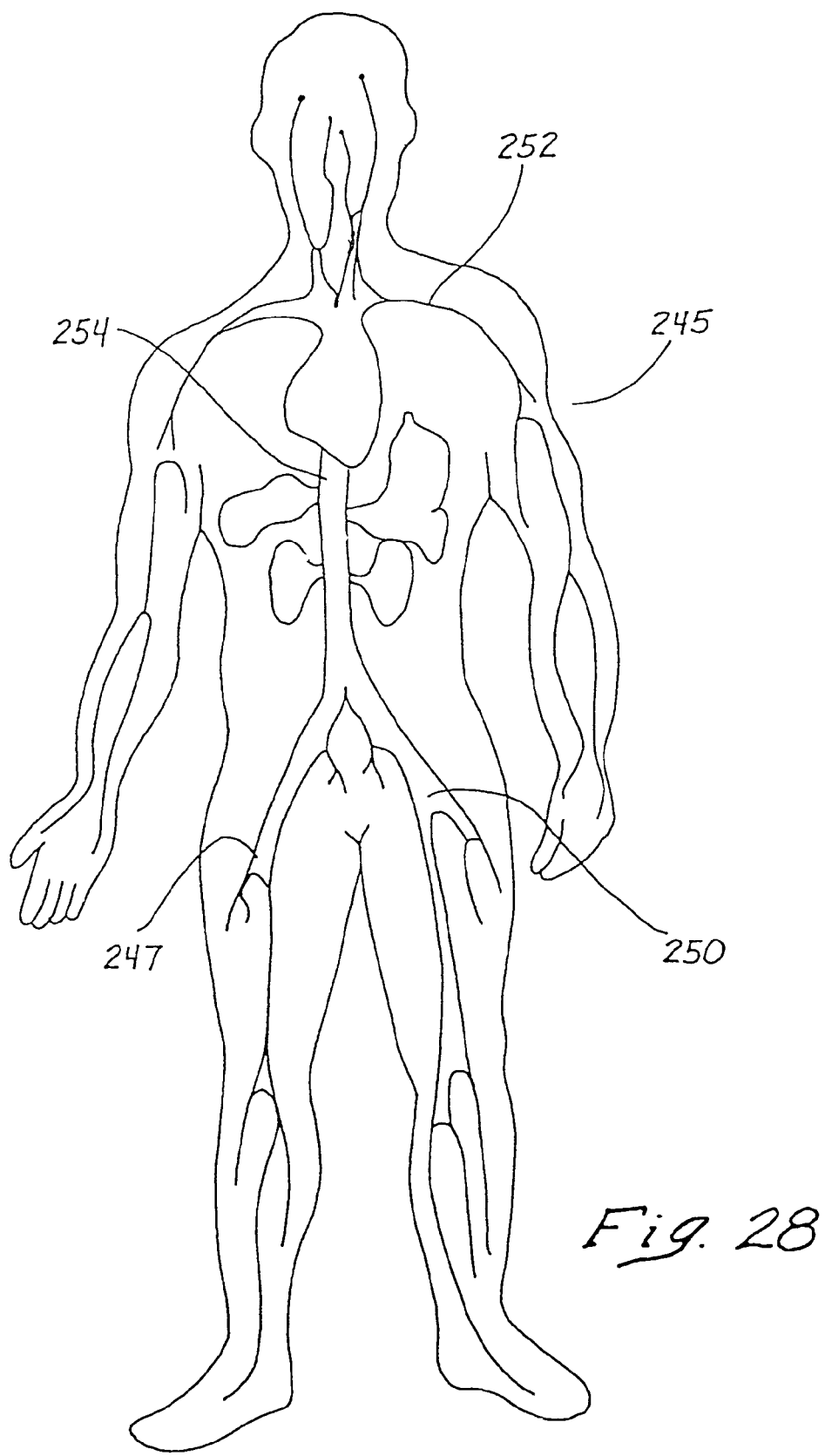
FIG. 28 is a top-plan view of a patient illustrating portions of the blood circulatory system.

Each of the foregoing embodiments of the heat exchange catheter 10 is adapted for use in cooling the entire human body, or perhaps only a portion of the total body. Methods of operation will vary widely depending on the focus of a particular procedure. By way of example, it will be noted with reference to FIG. 28 that the catheter 10 is particularly adapted for cooling blood in a procedure which may involve as many as three of the catheters 10. In FIG. 28, a human body 245 is illustrated along with a portion of the blood circulatory system including a pair of femoral veins 247, 250 and a subclavian vein 252. These veins 247, 250 and 252 all extend into the vena cava 254 of the body 245. In this procedure, separate catheters, such as the heat exchange catheter 10, can be introduced into each of the femoral veins 247, 250 and the subclavian vein 252 with their respective heat exchange regions disposed in the vena cava 254. Alternatively, and preferably, only two such catheters would be introduced from two of the three veins 247, 250 and 252.

A systemic version of the catheter might have a diameter in a range of between 9 and 15 French, and a length of approximately 20 to 80 centimeters long. It is contemplated that this design could conceivably cool the body in several hours. The use of two such catheters inserted into the vena cava 254 as mentioned above could be expected to reduce the time required to cool the body by a factor of 2. It will be appreciated that similar catheters and methods can be used to lower the temperature of blood in the native carotid or in the vertebral circulatory system. The amount of blood heat lost is directly proportional to the temperature differential, the blood velocity and the blood-to-catheter surface area.

Particularly in an operative setting wherein the heat exchange catheter 10 is to be inserted into a blood vessel, a further design feature best illustrated in FIGS. 29-33 will be of particular interest. In these views, an introducer 256 is positioned for percutaneous insertion into a blood vessel such as the femoral vein 250. A sleeve 258 is provided on the catheter 10 and slidable along the outer tube 192 between two positions. The first position is illustrated in FIG. 29 wherein the sleeve 258 is disposed in a spaced relationship with the heat exchange region 47. The second position of the sleeve 258 is illustrated in FIG. 30 where the sleeve 258 covers the heat exchange region 47. In this position the balloons or fibers associated with the region 47 are compressed to a low profile state greatly facilitating introduction of the catheter 10 into the introducer 256. In addition, the covered heat exchange region 47 is stiffened for easier introduction into the introducer 256. The fibers and/or balloons are also protected from the interior surface of the introducer 256. Optionally, a stiffening mandril may be inserted down one or more of the tubes 190, 192 to facilitate introduction of the catheter 10 into the introducer 256.

After this initial insertion, the sleeve 258 remains within the introducer 256 while the remainder of the heat exchange region 47 is moved distally into the conduit as illustrated in FIG. 31. At this point, the sleeve 258 can be removed from the introducer 256 by sliding it proximally to its first position as illustrated in FIG. 33.

This method of introduction is facilitated by providing the sleeve 258 with a generally cylindrical configuration. The diameter of the cylindrical sheath should be less that the inside diameter of the introducer 256. However, at the proximal end of the sheath 258, an annular flange 261 or other enlargement can be provided to ensure that the sheath 258 does not pass beyond the introducer 256.

Another feature associated with the present invention relates to a blood clot basket or snare 263, best illustrated in FIGS. 34 and 35. This snare 263 is preferably positioned downstream of the heat exchange region 47 associated with the catheter 10. It being appreciated that any structure disposed in a blood vessel may tend to generate blood clots, it is the purpose of the snare 263 to capture any such clots. The snare 263 of the preferred embodiment includes a plurality of wires 265 which extend along a shaft 267 with their opposing ends fixed in the manifold 194 and a distal cap 270. The wires 265 in a preferred embodiment are formed of stainless steel or a nickel titanium alloy.

In the illustrated embodiment, the shaft 267 extends to the proximal end 43 of the catheter 10 either through the lumen of the inner tube 190 or alternatively through a second, separate lumen in the inner tube 190. In the former case, a seal would be required at the distal end of the manifold 194 to prevent any leakage of heat exchange fluid 85 around the shaft 267.

In either case, the shaft 267 is free to move relative to the concentric tubes 190- and 192. When the shaft 267 is moved relatively distally, the snare wires 265 are provided with a generally low profile. When the shaft 267 is moved relatively proximally, the wires 265 deploy to provide the snare with an enlarged high-profile configuration as illustrated in FIG. 35.

In a further embodiment of the snare 263, the wires 265 are connected to the manifold 194 and extend to distal ends which are unattached or free. The wires 265 in this embodiment, best illustrated in FIG. 36, are bent to a deployed enlarged configuration. With such an embodiment, insertion is facilitated by providing a delivery sheath which is movable to maintain the wires 265 in a low-profile state. Once the catheter 10 is in place, the sheath 262 can be removed thereby permitting the wires 265 to automatically expand to their enlarged high-profile state.

With respect to the forgoing disclosure as a whole, it will be apparent that many variations from these preferred embodiments will now be apparent to those skilled in the art. For example, with respect to the balloon embodiments previously discussed, it will be appreciated that the advantages of this invention can be derived with only a single balloon. On the other hand, there seem to be several advantages associated with multiple balloon embodiments. Notably, a more even and balanced transfer of heat exchange can be achieved with multiple balloons. In addition, there appears to be better mixing with respect to both the blood 31 as well as the heat exchange fluid 85. Multiple balloons also provide an increased surface area relative to single balloon embodiments. Furthermore, the overall flexibility of the catheter 10 is enhanced with multiple balloons separated by interruptions which provide natural flex points for the catheter. When the balloons experience the high perfusion pressure, they become more stiff. The reduced diameter interruptions provide for increased flexibility at these joints.

Additional flexibility can be derived by providing the shaft 40 with variable stiffness. This variability can be produced by different materials forming the shaft 40 along its length or alternatively, tapering or otherwise varying the diameter of the shaft 40. For example, the shaft 40 can be progressively tapered from its proximal end 43 to its distal end 45 in order to provide a softer and more flexible heat exchange region 47.

In any of the foregoing embodiments of the catheter 10, the inner tube 190 can be provided with a central lumen facilitating introduction over a guidewire and providing a capability for the infusion of fluids through the catheter 10.

With the intent of maximizing heat transfer with the body fluid in a conduit feeding a specific region of the body, any of the factors previously noted can be addressed to provide structural modifications to the foregoing embodiments. Of course changes in the material or size of any of the structural elements described can be varied to achieve various heat exchange properties. Realizing the many changes which might be contemplated, one is cautioned not to limit this concept only to the specific embodiments illustrated and disclosed, but rather to determine the scope of the invention with reference to the following claims.

The invention claimed is:

1. A heat exchange catheter comprising:
a catheter body having at least one heat exchange fluid lumen configured for fluid communication with heat exchange elements coupled to the catheter body for circulating heat exchange fluid through the catheter and heat exchange elements to exchange heat with the blood of a patient when the catheter is positioned in the bloodstream of the patient without the heat exchange fluid entering the bloodstream of a patient; and
a plurality of heat exchange elements communicating with the fluid lumen, each element defining an element body, a space being established between the catheter body and the element body such that blood can flow through the space between the element body and catheter body, the catheter body defining a diameter that is larger than a diameter of an element body, each element body not extending distally past the catheter body.

2. The catheter recited in claim 1, wherein each heat exchange element defines a respective proximal end and respective distal end, and the proximal and distal ends of the elements are connected to the catheter body.

3. The catheter of claim 1, wherein each heat exchange element defines a respective proximal end, a respective distal end, the element body being therebetween, the element body being spaced from the catheter body.

4. The catheter of claim 1, wherein the element bodies are spirally shaped.

5. A heat exchange catheter comprising:
a catheter body having at least one heat exchange fluid lumen configured for fluid communication and at least one heat exchange element defined upon the catheter body for circulating heat exchange fluid through the catheter and heat exchange element to exchange heat with the blood of a patient when the catheter is positioned in the bloodstream of the patient without the heat exchange fluid entering the bloodstream of a patient; and
wherein the heat exchange element communicates with the fluid lumen, the heat exchange element being externally fluted in a spiral configuration along at least a segment thereof, wherein the catheter body is closed in that fluid laterally outward of the heat exchange element upon the catheter body cannot flow between the heat exchange element and a long axis defined by the spiral configuration of the heat exchange element.

6. The catheter of claim 5, comprising plural heat exchange elements axially arranged along the body.

7. The catheter of claim 5, wherein the catheter is provided with distal metal structure.

8. A heat exchange catheter comprising:

a catheter body having at least one heat exchange fluid lumen configured for fluid communication and at least one heat exchange element distally located on the catheter body for circulating heat exchange fluid through the catheter and heat exchange element to exchange heat with the blood of a patient when the catheter is positioned in the bloodstream of the patient without the heat exchange fluid entering the bloodstream of a patient; and wherein the heat exchange element communicates with the fluid lumen, the heat exchange element being externally in a spiral configuration along at least a segment thereof, wherein fluid laterally outward of the heat exchange element cannot flow laterally past the heat exchange element between the heat exchange element and a long axis defined by the spiral configuration of the heat exchange element.

9. The catheter of claim 8, comprising plural heat exchange elements axially arranged along the body.

10. The catheter of claim 8, wherein the catheter is provided with distal metal structure.

* * * * *